(12) United States Patent  
Lee et al.

(10) Patent No.: US 12,419,660 B2  
(45) Date of Patent: Sep. 23, 2025

(54) END TOOL FOR SURGICAL INSTRUMENT AND METHOD OF MANUFACTURING THE SAME

(71) Applicant: LivsMed Inc., Seongnam-si (KR)

(72) Inventors: Jung Joo Lee, Seongnam-si (KR); Heejin Kim, Seongnam-si (KR); Dongkyu Jang, Seongnam-si (KR); Donghoon Kang, Seongnam-si (KR)

(73) Assignee: LIVSMED INC., Seongnam-si (KR)

( * ) Notice: Subject to any disclaimer, the term of this patent is extended or adjusted under 35 U.S.C. 154(b) by 471 days.

(21) Appl. No.: 17/869,121

(22) Filed: Jul. 20, 2022

(65) Prior Publication Data

US 2022/0354523 A1  Nov. 10, 2022

Related U.S. Application Data

(63) Continuation of application No. 17/539,835, filed on Dec. 1, 2021, now Pat. No. 11,426,188.

(30) Foreign Application Priority Data

Dec. 9, 2020 (KR) .................... 10-2020-0170980

(51) Int. Cl.  
*A61B 17/29* (2006.01)  
*A61B 17/00* (2006.01)

(52) U.S. Cl.  
CPC .... *A61B 17/29* (2013.01); *A61B 2017/00526* (2013.01); *A61B 2017/0084* (2013.01); *A61B 2017/2903* (2013.01); *A61B 2017/292* (2013.01); *A61B 2017/2936* (2013.01)

(58) Field of Classification Search  
CPC ............ A61B 17/29; A61B 2017/0084; A61B 2017/2903; A61B 2017/292; A61B 2017/2936  
See application file for complete search history.

(56) References Cited

U.S. PATENT DOCUMENTS

| | | | |
|---|---|---|---|
| 6,394,998 B1 | 5/2002 | Wallace et al. | |
| 2007/0089557 A1* | 4/2007 | Solomon | A61B 34/71 74/490.01 |
| 2007/0208375 A1 | 9/2007 | Nishizawa et al. | |
| 2010/0286480 A1 | 11/2010 | Peine et al. | |
| 2014/0330288 A1* | 11/2014 | Date | A61B 34/37 606/130 |
| 2015/0150635 A1* | 6/2015 | Kilroy | B25J 17/02 606/130 |

FOREIGN PATENT DOCUMENTS

| | | | |
|---|---|---|---|
| JP | 59-102587 A | 6/1984 | |
| JP | 2010-220786 A | 10/2010 | |

(Continued)

*Primary Examiner* — Tan-Uyen T Ho  
*Assistant Examiner* — Cherie M Poland  
(74) *Attorney, Agent, or Firm* — Bridgeway IP Law Group, PLLC; Sang Ho Lee; Hyun Woo Shin

(57) ABSTRACT

Provided are an end tool of a surgical instrument and a method of manufacturing the same, and more particularly, an end tool of a surgical instrument that may be manually operated to be used in laparoscopic surgery or other various surgery and a method of manufacturing the end tool, wherein a load applied to a pin (rotary shaft) and the pulley is appropriately distributed such that the pulley may be sufficiently rotated and at the same time, an overall durability may be improved.

14 Claims, 48 Drawing Sheets

(56) References Cited

FOREIGN PATENT DOCUMENTS

| | | | |
|---|---|---|---|
| JP | 2018-187029 | A | 11/2018 |
| JP | 2020-031771 | A | 3/2020 |
| KR | 10-2016-0008169 | A | 1/2016 |
| KR | 10-2122508 | B1 | 6/2020 |

* cited by examiner

END TOOL FOR SURGICAL INSTRUMENT AND METHOD OF MANUFACTURING THE SAME

CROSS-REFERENCE TO RELATED APPLICATION

The present application is a continuation of U.S. application Ser. No. 17/539,835 filed on Dec. 1, 2021, which claims priority under 35 U.S.C. § 119 to Korean patent application No. 10-2020-0170980 filed on Dec. 9, 2020, the entire disclosures of which are hereby incorporated by reference.

BACKGROUND

1. Field

The present disclosure relates to an end tool of a surgical instrument and a method of manufacturing the same, and more particularly, an end tool of a surgical instrument that may be operable manually to be used in laparoscopic surgery or other various surgeries, wherein the end tool has entirely improved durability while sufficiently rotating a pulley because a load applied to a pin (rotary shaft) and the pulley is appropriately distributed, and a method of manufacturing the end tool.

2. Description of the Related Art

Surgery denotes a process of curing illness by cutting, incising, or manipulating the skin, the mucosa layer, and other tissues by using a medical instrument. In addition, laparotomy that treats, shapes, or removes an organ by cutting and opening the skin of a surgical site may cause bleeding, side effects, pain of a patient, scar, etc. Therefore, surgery performed by inserting only a medical instrument, e.g., a laparoscope, a surgical instrument, a microscope for microsurgery, etc. after forming a predetermined hole in the skin, or surgery using a robot has been recently considered as an alternative.

A surgical instrument is an instrument having an end tool provided at an end of a shaft that passes through a hole in the skin, so that a doctor directly manipulates the end tool with his/her own hands via a predetermined driver or manipulates the end tool by using a robot arm to carry out an operation on a surgical site. The end tool provided at the surgical instrument performs a pivoting operation, a gripping operation, a cutting operation, etc. via a predetermined structure.

The above-mentioned background art is technical information possessed by the inventor for the derivation of the present disclosure or acquired during the derivation of the present disclosure, and cannot necessarily be said to be a known technique disclosed to the general public prior to the filing of the present disclosure.

SUMMARY

One or more embodiments include an end tool for a surgical instrument that is manually operable to be used in laparoscopic surgery or other various surgeries, wherein a load applied to a pin (rotary shaft) and a pulley is appropriately distributed such that the pulley rotates smoothly and durability may be overall improved, and a method of manufacturing the end tool.

Additional aspects will be set forth in part in the description which follows and, in part, will be apparent from the description, or may be learned by practice of the presented embodiments of the disclosure.

According to an embodiment, an end tool of a surgical instrument includes: at least one jaw formed to be rotatable; an end tool hub in which a first shaft that is a rotating center of the at least one jaw is coupled; a pitch hub axially coupled to the end tool hub and provided to be rotatable with respect to the end tool hub; and at least one pin assembly coupled to the pitch hub and formed to be rotatable in the pitch hub, wherein the pin assembly includes: a pulley formed in a loop shape and having a hollow portion formed therein; a pin inserted in the hollow portion of the pulley and performing as a rotary shaft; and a plurality of friction reducing members arranged between an inner circumferential surface of the pulley and the pin.

The plurality of friction reducing members and an outer circumferential surface of the pin may be in direct contact with each other.

The pin assembly may include two pulleys facing each other, which include a first outer pulley and a second outer pulley, and may further include a first inner pulley arranged at an inner side of the first outer pulley and a second inner pulley arranged at an inner side of the second outer pulley.

The first outer pulley, the first inner pulley, the second inner pulley, and the second outer pulley may be sequentially fitted onto the pin therethrough.

A spacer may be additionally interposed between the first inner pulley and the second inner pulley.

The end tool hub may be arranged between the first inner pulley and the second inner pulley.

The friction reducing members may be arranged in the first outer pulley and in the second outer pulley.

The friction reducing members may be arranged in the first inner pulley and in the second inner pulley.

A groove having a shape corresponding to each of the friction reducing members may be formed in an inner circumferential surface of the pulley.

A radius of the groove formed in the inner circumferential surface of the pulley may be equal to or greater than a radius of the friction reducing member.

Each of the friction reducing members may be at least partially accommodated in the groove such that the friction reducing member may not be removed from the pulley.

The end tool may further include a retainer formed as a loop shape and having at least one friction reducing member accommodation portion that is formed to have a shape corresponding to at least a part of each friction reducing member in a main body thereof.

Each friction reducing member may be inserted in each friction reducing member accommodation portion such that the friction reducing member is not removed from the pulley.

The friction reducing members may include balls.

The friction reducing members may include rollers.

According to another embodiment, a method of manufacturing an end tool for a surgical instrument includes: arranging a first outer pulley; arranging a plurality of friction reducing members in the first outer pulley; inserting a first replacement pin among the plurality of friction reducing members; fitting a first inner pulley onto the first replacement pin; fitting a second inner pulley onto the first replacement pin; arranging a second outer pulley; arranging a plurality of friction reducing members in the second outer pulley; inserting a second replacement pin among the plurality of friction reducing members; forming a pin assembly by transferring and fitting the second outer pulley and the plurality of friction reducing members, through which the second replacement pin passes, onto the first replacement pin.

The plurality of friction reducing members and an outer circumferential surface of the pin may be in direct contact with each other.

A groove having a shape corresponding to each of the friction reducing members may be formed in an inner circumferential surface of the first outer pulley or the second outer pulley.

The method may further include, after the arranging of the plurality of friction reducing members in the first outer pulley, fitting a retainer with the plurality of friction reducing members, the retainer being formed as a loop shape and having at least one friction reducing member accommodation portion that is formed to have a shape corresponding to at least a part of each friction reducing member in a main body thereof.

The method may further include, after the forming of the pin assembly, inserting the first outer pulley, the first inner pulley, the second inner pulley, and the second outer pulley, which are sequentially fitted onto the first replacement pin therethrough, entirely in a pitch hub; replacing the first replacement pin with a pin; and caulking an end portion of the pin.

Other aspects, features and advantages other than those described above will become apparent from the following detailed description of the drawings, claims and disclosure.

BRIEF DESCRIPTION OF THE DRAWINGS

The above and other aspects, features, and advantages of certain embodiments of the disclosure will be more apparent from the following description taken in conjunction with the accompanying drawings, in which.

DETAILED DESCRIPTION

Figure 1A:
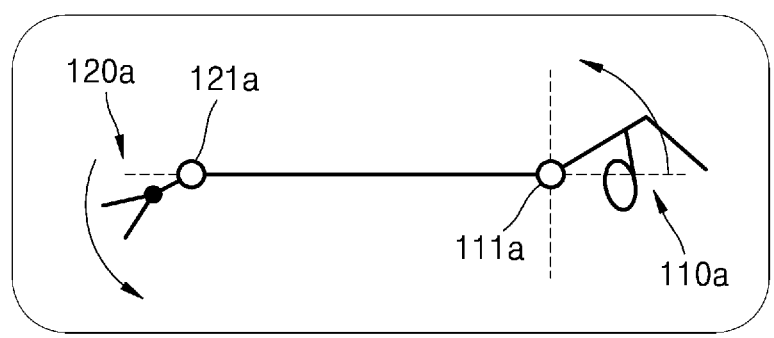
FIG. 1A is a conceptual diagram of pitch motion of a conventional surgical instrument.

The present disclosure may include various embodiments and modifications, and particular embodiments thereof are illustrated in the drawings and will be described herein in detail. However, it will be understood that the present disclosure is not limited to the embodiments and includes all modifications, equivalents, and replacements within the idea and technical scope of the present disclosure. Moreover, detailed descriptions related to well-known functions or configurations will be omitted in order not to unnecessarily obscure subject matters of the present disclosure.

Although terms such as "first" and "second" may be used herein to describe various elements or components, these elements or components should not be limited by these terms. These terms are only used to distinguish one element or component from other elements or components.

The terminology used herein is for explaining specific embodiments only and is not intended to limit the present disclosure. As used herein, the singular forms "a," "an", and "the" are intended to include the plural forms as well, unless the context clearly indicates otherwise. It will be understood that terms such as "comprise," "include," and "have," when used herein, specify the presence of state features, integers, steps, operations, elements, components, or combinations thereof, but do not preclude the presence or addition of one or more other features, integers, steps, operations, elements, components, or combinations thereof.

Hereinafter, embodiments of the present disclosure will be described in detail with reference to the accompanying drawings. In the following description, like reference numerals denote like elements, and redundant descriptions thereof will be omitted.

In addition, it will be understood that various embodiments of the present disclosure may be interpreted or implemented in combination, and technical features of each embodiment may be interpreted or implemented in combination with technical features of other embodiments.

An instrument for surgery of the present disclosure is characterized in that if a manipulation part is rotated in one direction for at least any one of pitch, yaw, and actuation motions, an end tool is rotated in intuitively the same direction as the direction in which the manipulation part is manipulated.

Figure 1B:
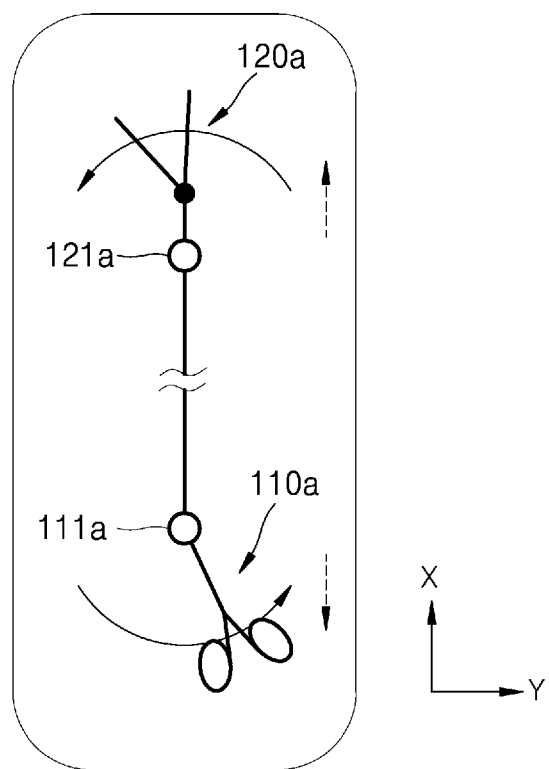
FIG. 1B is a conceptual diagram of yaw motion.

FIG. 1A is a schematic view illustrating pitch motion of an instrument for surgery of the related art, and FIG. 1B is a schematic view illustrating yaw motion of the instrument for surgery of the related art.

Referring to FIG. 1A, a pitch motion of the instrument for surgery of the related art is performed as follows. In a state in which an end tool 120a is in front of an end tool rotation center 121a and a manipulation part 110a is in back of a manipulation part rotation center 111a, if the manipulation part 110a is rotated clockwise, the end tool 120a is also rotated clockwise, and if the manipulation part 110a is rotated counterclockwise, the end tool 120a is also rotated counterclockwise. Referring to FIG. 1B, a yaw motion of the instrument for surgery of the related art is performed as follows. In a state in which the end tool 120a is in front of the end tool rotation center 121a and the manipulation part 110a is in back of the manipulation part rotation center 111a, if the manipulation part 110a is rotated clockwise, the end tool 120a is also rotated clockwise, and if the manipulation part 110a is rotated counterclockwise, the end tool 120a is also rotated counterclockwise. In this case, from the viewpoint of a horizontal direction of a user, when the user moves the manipulation part 110a to the left, the end tool 120a moves to the right, and when the user moves the manipulation part 110a to the right, the end tool 120a moves to the left. Consequently, since the manipulation direction of the user and the operation direction of the end tool are opposite each other, the user may make mistakes and have difficulty in manipulation.

Figure 1C:
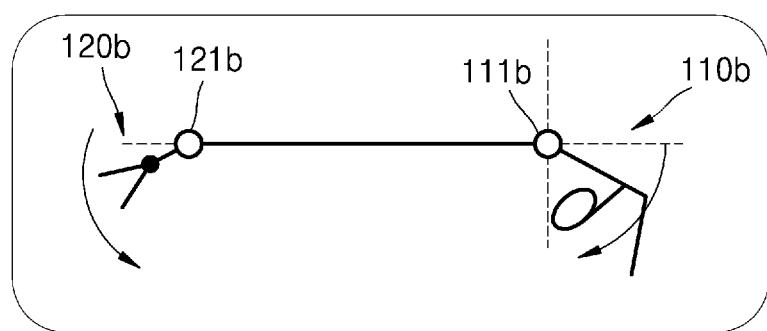
FIG. 1C is a conceptual diagram of pitch motion of another conventional surgical instrument.
Figure 1D:
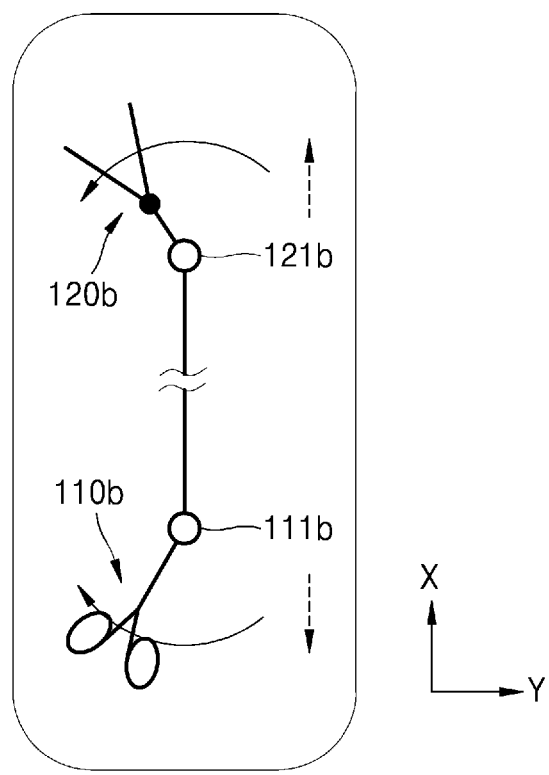
FIG. 1D is a conceptual diagram of yaw motion.

FIG. 1C is a schematic view illustrating a pitch motion of another instrument for surgery of the related art, and FIG. 1D is a schematic view illustrating a yaw motion of the instrument for surgery of the related art.

Figure 1E:
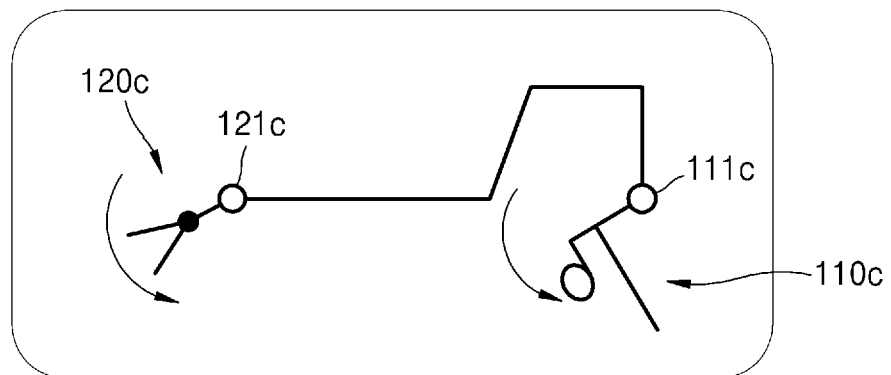
FIG. 1E is a conceptual diagram of pitch motion of a surgical instrument according to the present disclosure.
Figure 1F:
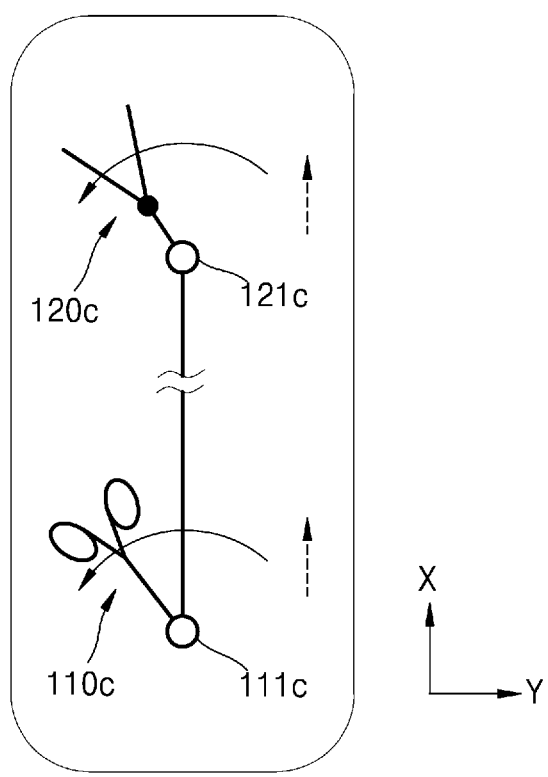
FIG. 1F is a conceptual diagram of yaw motion.

Referring to FIG. 1C, some instruments for surgery of the related art have a mirror-symmetric structure and perform a pitch motion as follows: in a state in which an end tool 120b is formed in front of an end tool rotation center 121b and an manipulation part 110b is formed in back of a manipulation part rotation center 111b, when the manipulation part 110b is rotated clockwise, the end tool 120b is rotated counterclockwise, and when the manipulation part 110b is rotated counterclockwise, the end tool 120b is rotated clockwise. In this case, from the viewpoint of the rotation directions of the manipulation part 110b and the end tool 120b, the direction in which a user rotates the manipulation part 110b is opposite the direction in which the end tool 120b is accordingly rotated. Consequently, the user may confuse manipulation directions, and the operation of a joint may not be intuitive, thereby causing mistakes. In addition, referring to FIG. 1D, a yaw motion is performed as follows. In a state in which the end tool 120b is in front of the end tool rotation center 121b and the manipulation part 110b is in back of the manipulation part rotation center 111b, if the manipulation part 110b is rotated clockwise, the end tool 120b is rotated counterclockwise, and if the manipulation part 110b is rotated counterclockwise, the end tool 120b is rotated clockwise. In this case, from the viewpoint of the rotation directions of the manipulation part 110b and the end tool 120b, the direction in which a user rotates the manipulation part 110b is opposite the direction in which the end tool 120b is accordingly rotated. Consequently, the user may confuse manipulation directions, and the operation of the joint may not be intuitive, thereby causing mistakes. As described above, when a user performs a pitch or yaw motion of an instrument for surgery of the related art, the manipulation direction of the user is not the same as the operation direction of an end tool from the viewpoint of the rotation directions or the horizontal direction. This is because an end tool and a manipulation part of an instrument for surgery of the related art have different joint structures. That is, the end tool is formed in front of the rotation center of the end tool, whereas the manipulation part is formed in back of the rotation center of the manipulation part. In order to address this problem, instruments for surgery according to embodiments of the present disclosure illustrated in FIGS. 1E and 1F are characterized in that an end tool 120c is provided in front of an end tool rotation center 121c and a manipulation part 110c is also provided in front of a manipulation part rotation center 111c, such that the operations of the manipulation part 110c and the end tool 120c are intuitively identical to each other. In other words, unlike the configuration example of the related art in which the manipulation part is adjacent to a user (i.e., distant from the end tool) based on a joint thereof as illustrated in FIGS. 1A, 1B, 1C, and 1D, the instruments for surgery according to the embodiments of the present disclosure illustrated in FIGS. 1E and 1F are configured such that at least a portion of the manipulation part may be more adjacent to the end tool based on a joint thereof (i.e., than the joint thereof is to the end tool) at at least a moment of manipulation.

In other words, in the case of an instrument for surgery of the related art as illustrated in FIGS. 1A, 1B, 1C, and 1D, since an end tool is located in front of a rotation center thereof but a manipulation part is located in back of a rotation center thereof, the end tool fixed at a rear side thereof and configured to be moved at a front side thereof is moved by the manipulation part fixed at a front side thereof and configured to be moved at a rear side thereof, and thus the structures of the manipulation part and the end tool are not intuitively identical to each other. Therefore, the manipulation of the manipulation part and the operation of the end tool are not identical to each other from the viewpoint of the horizontal direction or rotation directions, and thus a user may be confused and may not intuitively quickly manipulate the manipulation part, thereby making mistakes. However, in the case of the instruments for surgery according to the embodiments of the present disclosure, since each of the end tool and the manipulation part moves with respect to a rear rotation center thereof, it may be considered that the operations of the end tool and the manipulation part are structurally intuitively identical to each other. In other words, like the end tool having a portion movable based on the rear rotation center thereof, the manipulation part has a portion movable based on the rear rotation center thereof. Thus, it may be considered that the operations of the end tool and the manipulation part are structurally intuitively identical to each other. Consequently, a user may intuitively rapidly control the direction of the end tool, and the possibility that the user makes a mistake may be significantly reduced. A specific mechanism enabling this function will be described below.

Figure 2:
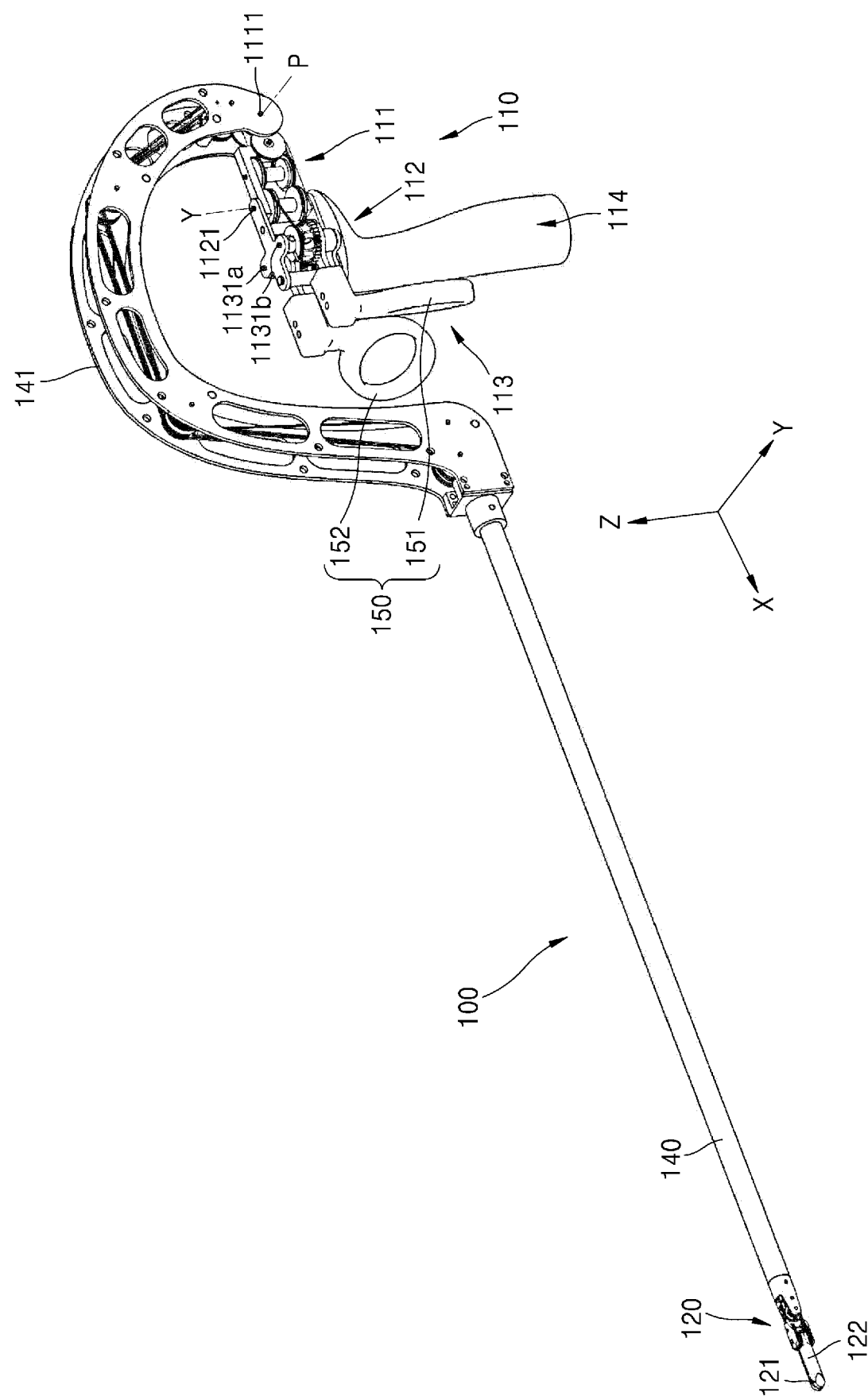
FIG. 2 is a perspective view illustrating a surgical instrument according to a first embodiment of the present disclosure.
Figure 3:
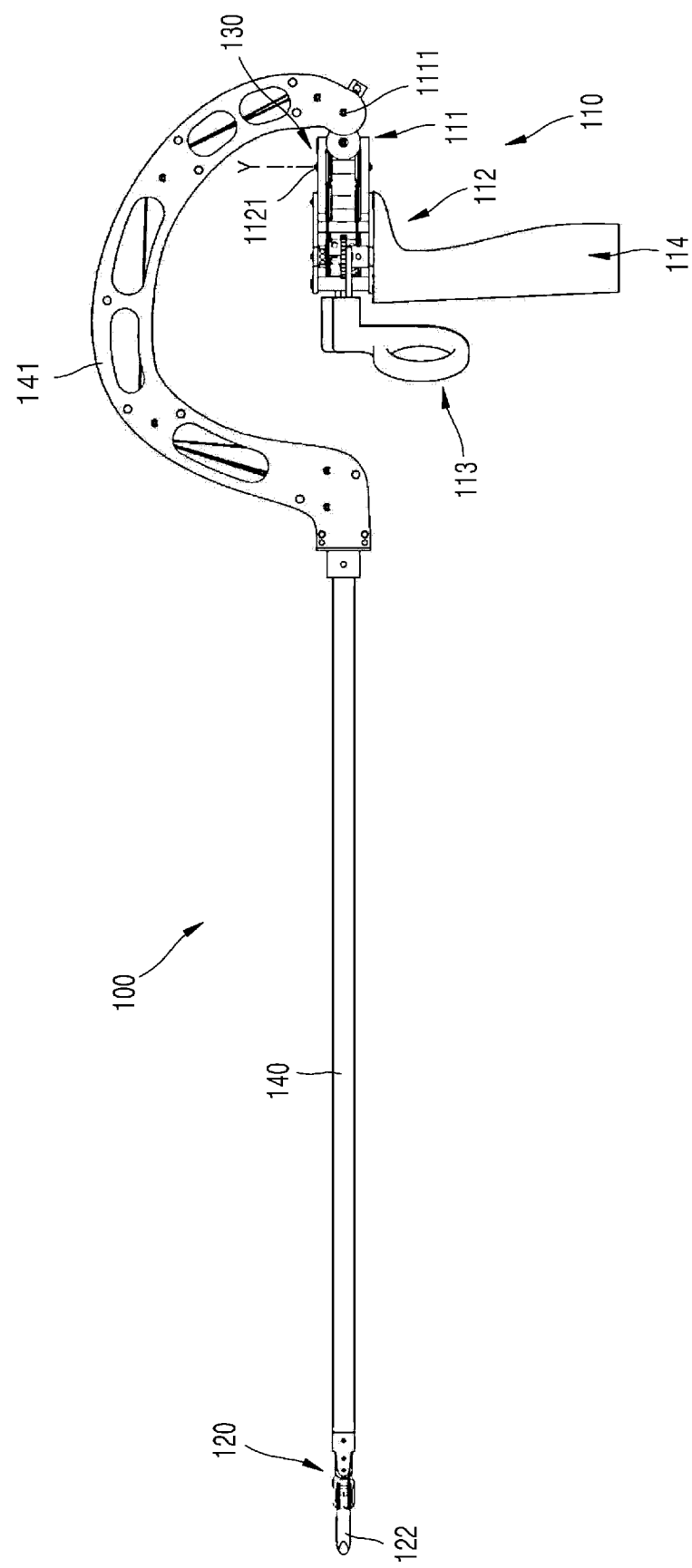
FIG. 3 is a side view of the surgical instrument of FIG. 2.

FIG. 2 is a perspective view illustrating an instrument for surgery according to a first embodiment of the present disclosure, and FIG. 3 is a side view illustrating the instrument for surgery shown in FIG. 2.

Referring to FIGS. 2, and 3, the instrument 100 for surgery according to the first embodiment of the present disclosure includes a manipulation part 110, an end tool 120, a power transmission part 130, a connecting part 140, and a ring handle 150. Here, the connecting part 140 may have a hollow shaft shape accommodating at least one wire (described later). The manipulation part 110 may be coupled to one end portion of the connecting part 140, and the end tool 120 may be coupled to the other end portion of the connecting part 140 such that the manipulation part 110 and the end tool 120 may be connected through the connecting part 140. Here, the connecting part 140 of the instrument 100 for surgery according to the first embodiment of the present disclosure is characterized by having a bent part 141 on a side of the manipulation part 110. As described above, an end portion of the connecting part 140 located on a side of the manipulation part 110 is bent such that a pitch manipulation part 111, a yaw manipulation part 112, and an actuation manipulation part 113 may be located on or adjacent to an extension line of the end tool 120. From another perspective, it may be stated that at least portions of the pitch manipulation part 111 and the yaw manipulation part 112 is accommodated in a concave region formed by the bent part 141. Owning to the shape of the bent part 141, the shapes and operations of the manipulation part 110 and the end tool 120 may be more intuitively identical to each other.

In addition, a plane formed by the bent part 141 may be substantially the same as a pitch plane, that is, an XZ plane shown in FIG. 2. In this manner, since the bent part 141 is provided on the same plane as the XZ plane, interference between manipulation parts may be reduced. Alternatively, any other configuration of the end tool and the manipulation part may be possible in addition to the XZ plane configuration.

The manipulation part 110 is provided on one end portion of the connecting part 140 and has an interface such as a tweezers shape, a stick shape, or a lever shape that a surgeon may directly manipulate, such that if an surgeon manipulates the interface, the end tool 120 connected to the interface and inserted into the body of a patient may be operated for surgery. Although FIG. 2 illustrates that the manipulation part 110 has a handle shape configured to be rotated by inserting a finger thereinto, the idea of the present disclosure is not limited thereto. That is, the manipulation part 110 may have any shape as long as the end tool 120 is connected to the manipulation part 110 and manipulated using the manipulation part 110.

The end tool 120 is provided on the other end portion of the connecting part 140 and is configured to be moved for surgery in a state in which that end tool 120 is inserted into a surgical site. As an example of the end tool 120, a pair of jaws 121 and 122 for gripping may be used as illustrated in FIG. 2. However, the idea of the present disclosure is not limited thereto. That is, various devices for surgery may be used as the end tool 120. For example, a device such as a one-armed cauter may be used as the end tool 120. The end tool 120 is connected to the manipulation part 110 through the power transmission part 130 to receive a driving force of the manipulation part 110 through the power transmission part 130, thereby performing a necessary surgical motion such as gripping, cutting, or suturing.

Herein, the end tool 120 of the instrument 100 for surgery of the first embodiment of the present disclosure is configured to rotate in at least two directions. For example, the end tool 120 may be capable of pitch motion around a Y axis of FIG. 2 and yaw motion and actuation motion around a Z axis of FIG. 2.

In the present disclosure, pitch, yaw, and actuation motions are defined as follows.

First, the pitch motion refers to upward and downward rotations of the end tool 120 with respect to an extension direction (the direction of an X axis in FIG. 2) of the connecting part 140, that is, rotation of the end tool 120 around the Y axis in FIG. 2. In other words, the pitch motion refers to upward and downward rotations of the end tool 120, which extends from the connecting part 140 in the extension direction (the X-axis direction in FIG. 2) of the connecting part 140, around the Y axis with respect to the connecting part 140. Next, the yaw motion refers to leftward and rightward rotations of the end tool 120 with respect to the extension direction (the X-axis direction in FIG. 2) of the connecting part 140, that is, rotation of the end tool 120 around the Z axis in FIG. 2. In other words, the yaw motion refers to leftward and rightward rotations of the end tool 120, which extends from the connecting part 140 in the extension direction (the X-axis direction in FIG. 2) of the connecting part 140, around the Z axis with respect to the connecting part 140. That is, the yaw motion refers to a motion in which the two jaws 121 and 122 of the end tool 120 are rotated around the Z axis in the same direction. In addition, the actuation motion refers to a motion in which the end tool 120 rotates around the same rotation axis as the yaw motion but the two jaws 121 and 122 rotate in opposite directions to move close to each other or away from each other. That is, the actuation motion refers to a motion in which the two jaws 121 and 122 rotate around the Z axis in opposite directions.

The power transmission part 130 may connect the manipulation part 110 and the end tool 120 to each other and transmit a driving force of the manipulation part 110 to the end tool 120. The power transmission part 130 may include a plurality of wires, pulleys, links, nodes, and gears. According to the embodiment of the present disclosure, the power transmission part 130 of the instrument 100 for surgery may include a pitch wire 130P, a first jaw wire 130J1, and a second jaw wire 130J2.

The ring handle 150 includes a first ring handle 151 and a second ring handle 152, and each of the ring handles 151 and 152 includes a fixed ring portion 153 and a variable ring portion 154. In an embodiment of the present disclosure, the instrument 100 for surgery includes the variable ring portions 154 for adjusting the sizes of holes of rings according to the sizes of fingers of a user such that the fingers of the user may be fitted into or tightly coupled to the ring handle 150, thereby improving convenience in manipulation for users. This will be described later in more detail. Hereinafter, parts of the instrument 100 for surgery shown in FIG. 2 such as the manipulation part 110, the end tool 120, and the power transmission part 130 will be described in more detail.

Figure 4:
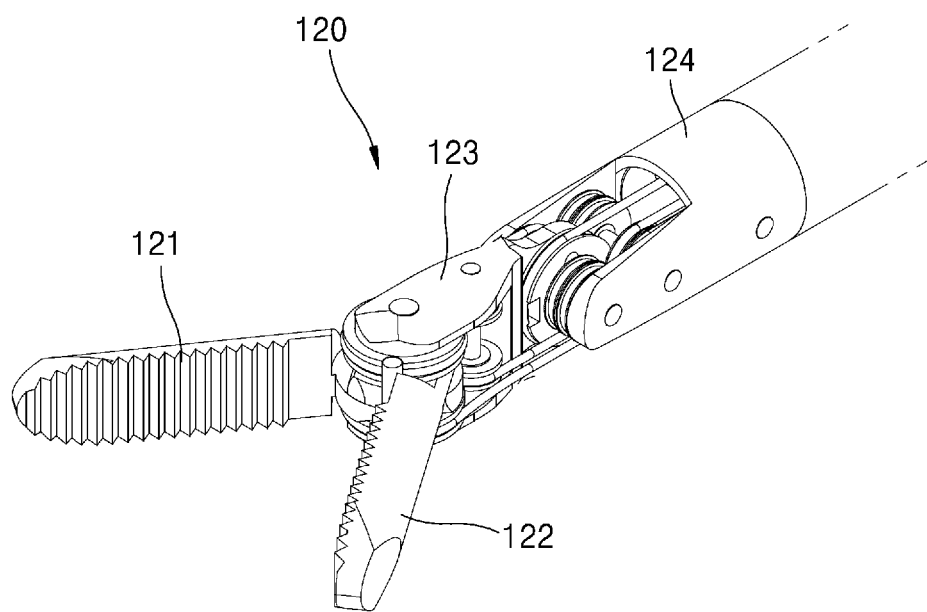
FIGS. 4 and 5 are perspective views illustrating an end tool of the surgical instrument of FIG. 2.
Figure 5:
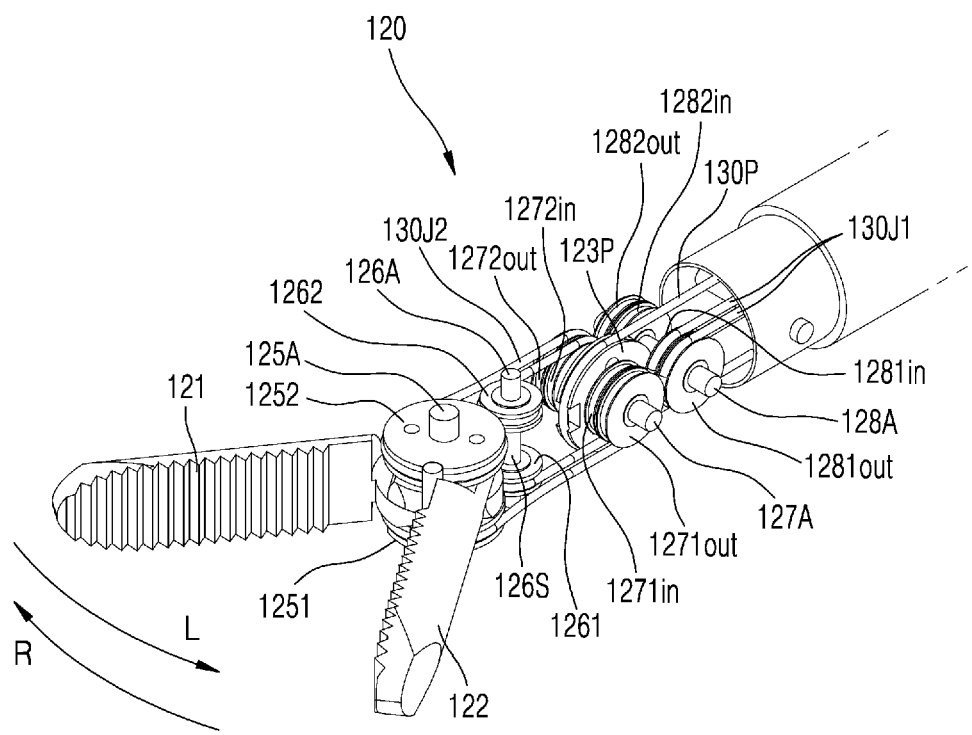
Figure 6:
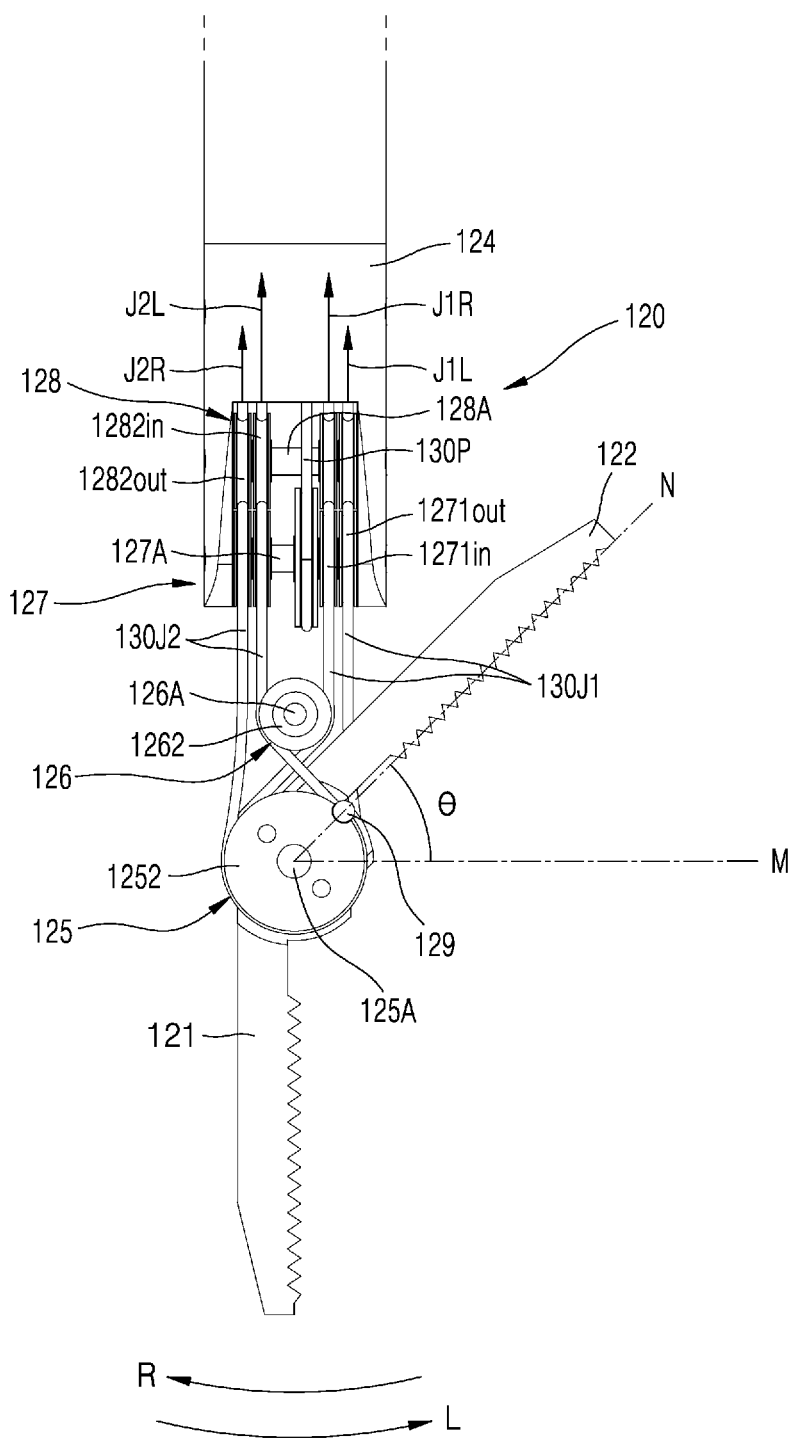
FIG. 6 is a plan view illustrating the end tool of the surgical instrument of FIG. 2.

FIGS. 4 and 5 are perspective views illustrating the end tool of the instrument for surgery shown in FIG. 2, and FIG. 6 is a plan view illustrating the end tool of the instrument for surgery shown in FIG. 2.

Referring to FIGS. 4, 5 and 6, the end the end tool 120 of the first embodiment of the present disclosure includes a pair of jaws 121 and 122, that is, a first jaw 121 and a second jaw 122 for gripping motion. In addition, the end tool 120 includes: a first pin first jaw pulley 1251, a third pin first external pulley 1271*out*, a fourth pin first external pulley 1281*out*, a third pin first internal pulley 1271*in*, and a fourth pin first internal pulley 1281*in* that are related to the rotation motion of the first jaw 121; and a first pin second jaw pulley 1252, a third pin second external pulley 1272*out*, a fourth pin second external pulley 1282*out*, a third pin second internal pulley 1272*in*, and a fourth pin second internal pulley 1282*in* that are related to the rotation motion of the second jaw 122. In this case, the first jaw 121, the first pin first jaw pulley 1251, the third pin first external pulley 1271*out*, the third pin first internal pulley 1271*in*, the second jaw 122, the first pin second jaw pulley 1252, the third pin second external pulley 1272*out*, and the third pin second internal pulley 1272*in* may be configured to rotate around an third pin 127A.

In addition, A pitch hub 124 is provided on an end portion of the connecting part 140 coupled to the end tool 120. The third pin first external pulley 1271*out*, the fourth pin first external pulley 1281*out*, the third pin first internal pulley 1271*in*, the fourth pin first internal pulley 1281*in*, the third pin second external pulley 1272*out*, the fourth pin second external pulley 1282*out*, the third pin second internal pulley 1272*in*, and the fourth pin second internal pulley 1282*in* are connected to the pitch hub 124.

Although it is illustrated that pulleys facing each other are parallel to each other, the idea of the present disclosure is not limited thereto. That is, the pulleys may have various positions and sizes suitable for the configuration of the end tool.

The first pin first jaw pulley 1251 and the first pin second jaw pulley 1252 face each other and rotate independently around a first pin 125A. Here, the first jaw 121 may be fixedly coupled to the first pin first jaw pulley 1251 so as to be rotated together with the first pin first jaw pulley 1251, and the second jaw 122 may be fixedly coupled to the first pin second jaw pulley 1252 so as to be rotated together with the first pin second jaw pulley 1252. Yaw and actuation motions of the end tool 120 are performed as according to rotations of the first pin first jaw pulley 1251 and the first pin second jaw pulley 1252. That is, yaw motion is performed when the first pin first jaw pulley 1251 and the first pin second jaw pulley 1252 are rotated in the same direction, and actuation motion is performed when the first pin first jaw pulley 1251 and the first pin second jaw pulley 1252 are rotated in opposite directions.

In addition, a second pin first jaw pulley 1261 and a second pin second jaw pulley 1262 may be additionally provided as auxiliary pulleys on a side of the first pin first jaw pulley 1251 and the first pin second jaw pulley 1252, and the auxiliary pulleys may be rotatable on an second pin 126A. Although it is illustrated that the second pin first jaw pulley 1261 and the second pin second jaw pulley 1262 are configured to rotate on the single second pin 126A, the auxiliary pulleys may be configured to rotate on separate shafts, respectively. In other words, the second pin first jaw pulley 1261 being an auxiliary pulley may be placed between the first pin first jaw pulley 1251 and the third pin first external pulley 1271*out*/the third pin first internal pulley 1271*in*. In addition, the second pin second jaw pulley 1262 being an auxiliary pulley may be placed between the first pin second jaw pulley 1252 and the third pin second external pulley 1272*out*/the third pin second internal pulley 1272*in*. The auxiliary pulleys will be described later in more detail.

Elements related to rotation of the first pin first jaw pulley 1251 will be described below.

The third pin first external pulley 1271*out* and the third pin first internal pulley 1271*in* are placed to face each other at a side of the first pin first jaw pulley 1251. In this case, the third pin first external pulley 1271*out* and the third pin first internal pulley 1271*in* are independently rotatable about the third pin 127A. In addition, the fourth pin first external pulley 1281*out* and the fourth pin first internal pulley 1281*in* are placed to face each other respectively at sides of the third pin first external pulley 1271*out* and the third pin first internal pulley 1271*in*. Here, the fourth pin first external pulley 1281*out* and the fourth pin first internal pulley 1281*in* are independently rotatable around the Y-axis direction. Although it is illustrated that all of the third pin first external pulley 1271*out*, the fourth pin first external pulley 1281*out*, the third pin first internal pulley 1271*in*, and the fourth pin first internal pulley 1281*in* are rotatable around the Y-axis direction, the idea of the present disclosure is not limited thereto, and the rotating axes of the respective pulleys may be oriented in various directions according to configurations thereof.

The first jaw wire 130J1 may be sequentially wound to make contact with at least portions of the fourth pin first external pulley 1281*out*, the third pin first external pulley 1271*out*, the first pin first jaw pulley 1251, the second pin first jaw pulley 1261, the third pin first internal pulley 1271*in*, and the fourth pin first internal pulley 1281*in*, and the first jaw wire 130J1 may move along the pulleys while rotating the pulleys.

Thus, when the first jaw wire 130J1 is pulled in the direction of an arrow J1R in FIG. 6, the first jaw wire 130J1 rotates the fourth pin first internal pulley 1281*in*, the third pin first internal pulley 1271*in*, the second pin first jaw pulley 1261, the first pin first jaw pulley 1251, the third pin first external pulley 1271*out*, and the fourth pin first external pulley 1281*out*. At this time, as the first pin first jaw pulley 1251 is rotated in the direction of an arrow R in FIG. 6, the first pin first jaw pulley 1251 rotates the first jaw 121.

On the other hand, when the first jaw wire 130J1 is pulled in the direction of an arrow J1L in FIG. 6, the first jaw wire 130J1 rotates the fourth pin first external pulley 1281*out*, the third pin first external pulley 1271*out*, the first pin first jaw pulley 1251, the second pin first jaw pulley 1261, the third pin first internal pulley 1271*in*, and the fourth pin first internal pulley 1281*in*. At this time, as the first pin first jaw pulley 1251 is rotated in the direction of an arrow L in FIG. 6, the first pin first jaw pulley 1251 rotates the first jaw 121.

Hereinafter, the auxiliary pulleys 1261 and 1262 will be described in more detail.

The second pin first jaw pulley 1261 and second pin second jaw pulley 1262 may be in contact with the first jaw wire 130J1 and the second jaw wire 130J2, thereby changing paths of the first jaw wire 130J1 and the second jaw wire 130J2 to some degree and extending the rotation radii of the first jaw 121 and the second jaw 122. That is, according to the embodiment of the present disclosure, the second pin first jaw pulley 1261 and second pin second jaw pulley 1262 are additionally provided such that the maximum rotation angle may be increased by $\theta$ as illustrated in FIG. 6. This allows the two jaws of the end tool 120 to move away from each other for actuation motion in a state in which the two jaws are rotated together by 90° in yaw motion in the direction L. That is, this is because it is possible to further rotate the second jaw 122 by an additional angle $\theta$ as illustrated in FIG. 6. Similarly, actuation motion is also possible in a state in which the two jaws are rotated in yaw motion in the direction R. In other words, owing to the second pin first jaw pulley 1261 and second pin second jaw pulley 1262, the range of yaw motion in which actuation motion is possible may be increased. This will now be described in more detail.

In detail, in the instrument 100 for surgery according to the embodiment of the present disclosure, the second pin first jaw pulley 1261 and the second pin second jaw pulley 1262 are additionally arranged as auxiliary pulleys at a side of the first pin first jaw pulley 1251 and the first pin second jaw pulley 1252. In this manner, since the second pin first jaw pulley 1261 and the second pin second jaw pulley 1262 are arranged to change the paths of the first jaw wire 130J1 and the second jaw wire 130J2 to some degree and thus to change tangential directions of the first jaw wire 130J1 and the second jaw wire 130J2, a fixation coupling part of the second jaw wire 130J2 and the first pin second jaw pulley 1252 may be rotated up to a line N of FIG. 6. That is, the fixation coupling part of the second jaw wire 130J2 and the first pin second jaw pulley 1252 may be rotated until the coupling part is located on a common internal tangent of the first pin second jaw pulley 1252 and the second pin second jaw pulley 1262. Similarly, a coupling part of the first jaw wire 130J1 and the first pin first jaw pulley 1251 may be rotated until the coupling part is located on an common internal tangent of the first pin first jaw pulley 1251 and the second pin first jaw pulley 1261, thereby extending the range of rotation in the direction R.

In this manner, according to the present disclosure, the rotation radii of the first jaw 121 and the second jaw 122 may be increased, thereby obtaining an effect of increasing the range of yaw motion in which actuation motion is normally performed for opening and closing.

Next, elements relating to the rotation of the first pin second jaw pulley 1252 will be described.

The third pin second external pulley 1272*out* and the third pin second internal pulley 1272*in* are placed to face each other at a side of the first pin second jaw pulley 1252. Here, the third pin second external pulley 1272*out* and the third pin second internal pulley 1272*in* are independently rotatable around the third pin 127A. In addition, the fourth pin second external pulley 1282*out* and the fourth pin second internal pulley 1282*in* are placed to face each other at a side of the third pin second external pulley 1272*out* and the third pin second internal pulley 1272*in*. Here, the fourth pin second external pulley 1282*out* and the fourth pin second internal pulley 1282*in* are independently rotatable around the Y-axis direction. Although it is illustrated that all of the third pin second external pulley 1272*out*, the fourth pin second external pulley 1282*out*, the third pin second internal pulley 1272*in*, and the fourth pin second internal pulley 1282*in* are rotatable around the Y-axis direction, the idea of the present disclosure is not limited thereto, and the rotating axes of the respective pulleys may be oriented in various directions according to configurations thereof.

The second jaw wire 130J2 may be sequentially wound to make contact with at least portions of the fourth pin second external pulley 1282*out*, the third pin second external pulley 1272*out*, the first pin second jaw pulley 1252, the second pin second jaw pulley 1262, the third pin second internal pulley 1272*in*, and the fourth pin second internal pulley 1282*in*, and the second jaw wire 130J2 may move along the pulleys while rotating the pulleys.

Therefore, when the second jaw wire 130J2 is pulled in the direction of an arrow J2R of FIG. 6, the second jaw wire 130J2 rotates the fourth pin second external pulley 1282*out*, the third pin second external pulley 1272*out*, the first pin second jaw pulley 1252, the second pin second jaw pulley 1262, the third pin second internal pulley 1272*in*, and the fourth pin second internal pulley 1282*in*. At this time, as the first pin second jaw pulley 1252 is rotated in the direction of the arrow R of FIG. 6, the first pin second jaw pulley 1252 rotates the second jaw 122.

On the other hand, when the second jaw wire 130J2 is pulled in the direction of an arrow J2L of FIG. 6, the second jaw wire 130J2 rotates the fourth pin second internal pulley 1282*in*, the third pin second internal pulley 1272*in*, the second pin second jaw pulley 1262, the first pin second jaw pulley 1252, the third pin second external pulley 1272*out*, and the fourth pin second external pulley 1282*out*. At this time, as the first pin second jaw pulley 1252 is rotated in the direction of the arrow L of FIG. 6, the J21 pulley rotates the second jaw 122.

In addition, if an end portion of the first jaw wire 130J1 is pulled in the direction of the arrow J1R of FIG. 6, and at the same time the other end portion of the first jaw wire 130J1 is pulled in the direction of the arrow J1L of FIG. 6 (that is, if both end portions of the first jaw wire 130J1 are pulled), since the first jaw wire 130J1 is wound around lower portions of the third pin first external pulley 1271*out* and the third pin first internal pulley 1271*in* that are rotatable around the third pin 127A as shown in FIG. 5, the first pin first jaw pulley 1251 to which the first jaw wire 130J1 is fixedly coupled, the first jaw 121, the first pin 125A, and an end tool hub 123, and the second jaw 122 connected thereto are all rotated counterclockwise around the third pin 127A, and as a result, the end tool 120 is rotated downward in pitch motion. At this time, since the second jaw 122 and the second jaw wire 130J2 fixedly coupled to the second jaw 122 is wound around upper portions of the third pin second external pulley 1272*out* and the third pin second internal pulley 1272*in* that are rotatable around the third pin 127A, both end portions of the second jaw wire 130J2 are respectively moved in directions opposite the directions of the arrows J2L and J2R.

In contract, if an end portion of the second jaw wire 130J2 is pulled in the direction of the arrow J2R of FIG. 6, and at the same time the other end portion of the second jaw wire 130J2 is pulled in the direction of the arrow J2L of FIG. 6, since the second jaw wire 130J2 is wound around the upper portions of the third pin second external pulley 1272*out* and the third pin second internal pulley 1272*in* that are rotatable around the third pin 127A as shown in FIG. 5, the first pin second jaw pulley 1252 to which the second jaw wire 130J1 is fixedly coupled, the second jaw 122, the first pin 125A, and the end tool hub 123, and the first jaw 121 connected thereto are all rotated clockwise around the third pin 127A, and as a result, the end tool 120 is rotated upward in pitch motion. At this time, since the first jaw 121 and the first jaw wire 130J1 fixedly coupled to the first jaw 121 are wound around the lower portions of the third pin first external pulley 1271*out* and the third pin first internal pulley 1271*in* that are rotatable around the third pin 127A, both end portions of the first jaw wire 130J1 are respectively moved in directions opposite the directions of the arrows J1L and J1R.

In addition, the end tool 120 of the instrument 100*b* for surgery may further include a pitch pulley 123P, the manipulation part 110 may further include a pitch wire end pulley 115P, and the power transmission part 130 may further include the pitch wire 130P. In detail, the pitch pulley 123P of the end tool 120 may be rotatable about the third pin 127A and may be fixedly coupled to the end tool hub 123. In addition, a pitch pulley of the manipulation part may be rotatable about a pitch rotation shaft and may be fixedly coupled to a pitch manipulation part (not shown). In addition, the pitch wire 130P may connect the pitch pulley 123P of the end tool 120 to the pitch pulley of the manipulation part.

Thus, if a user rotates a first handle 114 around a pitch rotation shaft 1111 while holding the first handle 114 of the manipulation part 110, a pitch pulley coupled to the first handle 114 is rotated around the pitch rotation shaft 1111, and the rotation of the pitch pulley is transmitted to the pitch pulley 123P of the end tool 120 through the pitch wire 130P to rotate the pitch pulley 123P. As a result, the end tool 120 is rotated, and a pitch motion is performed.

That is, since the instrument 100 for surgery according to the first embodiment of the present disclosure includes the pitch pulley 123P of the end tool 120, the pitch wire end pulley 115P of the manipulation part 110, and the pitch wire 130P of the power transmission part 130, a pitch motion driving force of the pitch manipulation part 111 may be more completely transmitted to the end tool 120, and thus reliability of motion may be improved.

Manipulation Part

Figure 7:
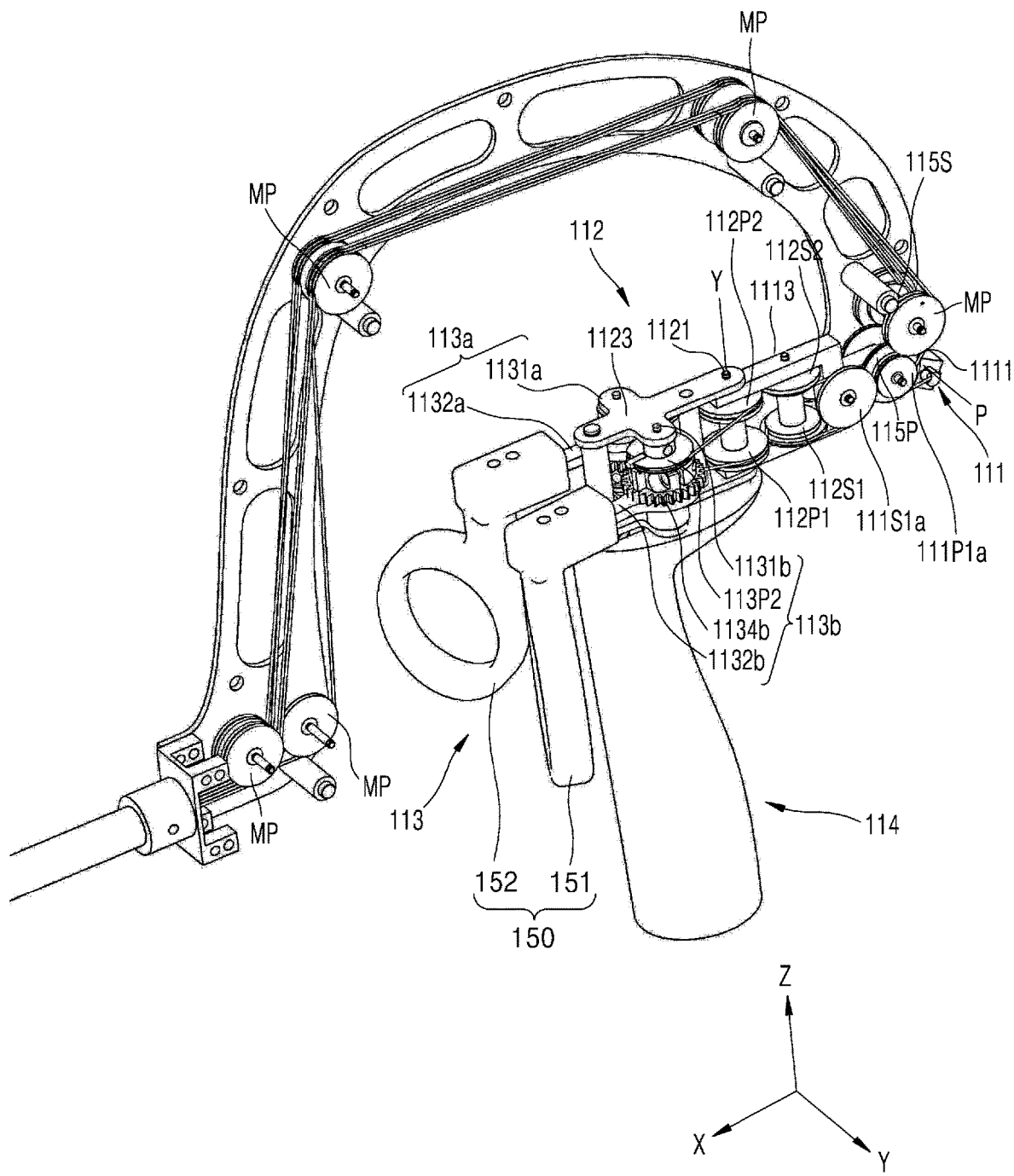
FIGS. 7 and 8 are perspective views illustrating a manipulation portion of the surgical instrument of FIG. 2.
Figure 8:
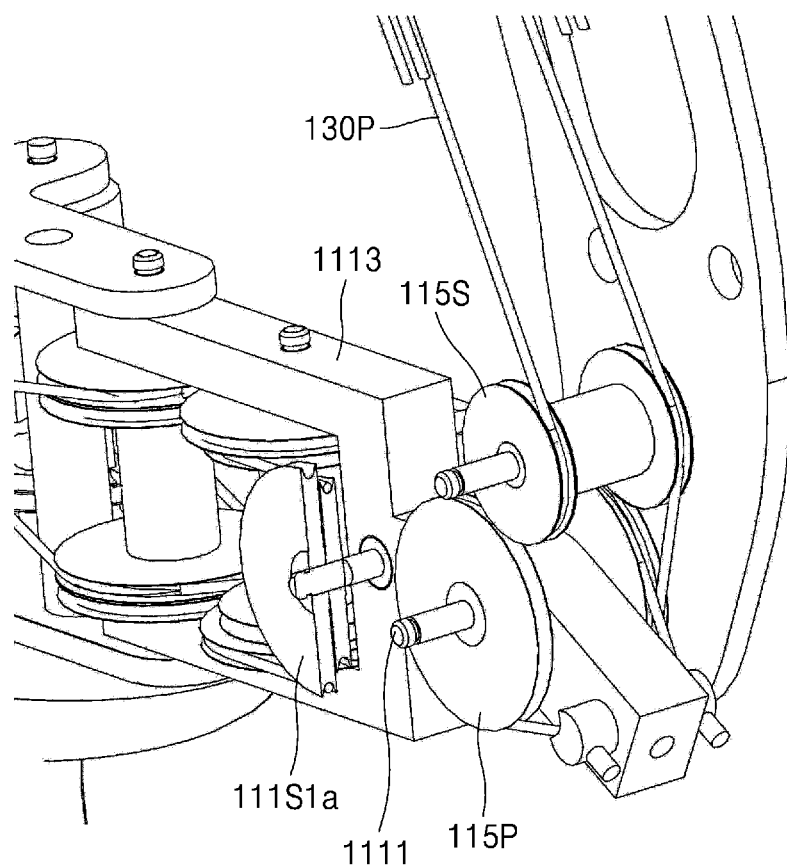

FIG. 7 and FIG. 8 are a perspective view illustrating the manipulation part of the instrument for surgery shown in FIG. 2.

Referring to FIG. 2 to FIG. 8, the manipulation part 110 of the instrument 100 for surgery includes the first handle 114 which a user may grip, the actuation manipulation part 113 configured to control actuation motion of the end tool 120, the yaw manipulation part 112 configured to control yaw motion of the end tool 120, and the pitch manipulation part 111 configured to control pitch motion of the end tool 120. In addition, the manipulation part 110 further includes the ring handle 150.

First, an example operation of the instrument 100 for surgery shown in FIG. 2 will be described. In a state in which a user holds the first handle 114 with his/her palm, the user may perform a pitch motion by rotating the first handle 114 around the Y axis (that is, around the pitch rotation shaft 1111) and a yaw motion by rotating the first handle 114 around the Z axis (that is, around a yaw rotation shaft 1121). In addition, in a state in which the user inserts his/her thumb and index finger in the ring handle 150 formed on an end of the actuation manipulation part 113, the user may rotate the actuation manipulation part 113 to perform an actuation motion.

Here, when the manipulation part 110 of the instrument 100 for surgery is rotated in a direction with respect to the connecting part 140, the end tool 120 is rotated intuitively in the same direction as the direction in which the manipulation part 110 is manipulated. In other words, if the first handle 114 of the manipulation part 110 is rotated in a certain direction, the end tool 120 is also rotated intuitively in the same direction as the certain direction, and thus a pitch motion or a yaw motion is performed. Here, the expression "intuitively in the same direction" may be used to denote that the direction in which a finger of a user holding the manipulation part 110 is moved is substantially the same as the direction in which a distal end portion of the end tool 120 is moved. The expression "intuitively in same direction" may not refer to completely in the same direction in a three-dimensional coordinate system. For example, it may be understood that the expression refers to sameness to the following extend: if a finger of a user is moved leftward, the distal end portion of the end tool 120 is also be moved leftward, and if the finger of the user is moved downward, the distal end portion of the end tool 120 is also moved downward.

To this end, in the instrument 100 for surgery of the first embodiment of the present disclosure, the manipulation part 110 and the end tool 120 are provided in the same direction with respect to a plane perpendicular to an extension axis (the X axis) of the connecting part 140. That is, when viewed based on a YZ plane of of FIG. 2, the manipulation part 110 extends in a positive (+) X-axis direction, and the end tool 120 also extends in the positive (+) X-axis direction. In other words, it may be stated that the formation direction of the end tool 120 on an end portion of the connecting part 140 is the same as the formation direction of the manipulation part 110 on the other end portion of the connecting part 140 based on the YZ plane. Furthermore, in other words, it may be stated that the manipulation part 110 is located in a direction away from the body of a user holding the manipulation part 110, that is, in a direction in which the end tool 120 is provided. That is, in the case of parts such as the first handle 114 and actuation rotation parts 1132a and 1132b which a user holds and moves for actuation, yaw, and pitch motions, each moving portion extends from the rotation center of a corresponding joint for the motions in the positive (+) X-axis direction. In this manner, the manipulation part 110 may be configured like the end tool 120 in which each moving portion extends from the rotation center of a corresponding joint for the motions in the positive (+) X-axis direction, and as described with reference to FIG. 1, a manipulation direction of a user may be identical to an operation direction of the end tool from the viewpoint of rotation directions and leftward and rightward directions. As a result, intuitively the same manipulation may be performed.

In detail, in the case of an instrument for surgery of the related art, a direction in which a user manipulates a manipulation part is different from a direction in which the end tool is actually operated, that is, intuitively different from the direction in which the end tool is actually operated. Thus, surgeons may not easily intuitively manipulate the instrument for surgery and may spend a long time to learn a skill of operating the end tool in desired directions. In some cases, patients may suffer from malfunctions.

In order to solve such problems, the instrument 100 for surgery of the first embodiment of the present disclosure is configured such that the manipulation direction of the manipulation part 110 and the operation direction of the end tool 120 are intuitively identical to each other. To this end, the manipulation part 110 is configured like the end tool 120. That is, in the manipulation part 110, portions that are actually moved for actuation, yaw, and pitch motions extend respectively from rotation centers of corresponding joints in the positive (+) X-axis direction. This will now be described in more detail.

The first handle 114 may be configured such that a user may grip the first handle 114 with his/her hand. In particular, a user may grip the first handle 114 by holding around the first handle 114 with his/her palm. In addition, the actuation manipulation part 113 and the yaw manipulation part 112 are provided above the first handle 114, and the pitch manipulation part 111 is provided at a side of the yaw manipulation part 112. In addition, another end portion of the pitch manipulation part 111 is connected to the bent part 141 of the connecting part 140.

The actuation manipulation part 113 includes a first actuation manipulation part 113a and a second actuation manipulation part 113b. The first actuation manipulation part 113*a* includes a first actuation rotation shaft 1131*a*, a first actuation rotation part 1132*a*, a first actuation pulley 113P1, and a first actuation gear 1134*a*. The second actuation manipulation part 113*b* includes a second actuation rotation shaft 1131*b*, a second actuation rotation part 1132*b*, a second actuation pulley 113P2, and a second actuation gear 1134*b*. Here, the ring handle 150 may be further formed on ends of the first and second actuation rotation parts 1132*a* and 1132*b* and may function as second handles.

Here, the actuation rotation shafts 1131*a* and 1131*b* may make a predetermined angle with an XY plane on which the connecting part 140 is located. For example, the actuation rotation shafts 1131*a* and 1131*b* may be parallel with the Z axis. In this state, if the pitch manipulation part 111 or the yaw manipulation part 112 is rotated, the coordinate system of the actuation manipulation part 113 may be relatively varied. However, the idea of the present disclosure is not limited thereto, and the actuation rotation shafts 1131*a* and 1131*b* may be oriented in various directions according to ergonomic designs for the hand structure of a user holding the actuation manipulation part 113.

In addition, the first actuation rotation part 1132*a*, the first actuation pulley 113P1, and the first actuation gear 1134*a* may be fixedly coupled to each other so as to be rotated together around the first actuation rotation shaft 1131*a*. Here, the first actuation pulley 113P1 may include a single pulley or two pulleys fixedly coupled to each other.

Similarly, the second actuation rotation part 1132*b*, the second actuation pulley 113P2, and the second actuation gear 1134*b* may be fixedly coupled to each other so as to be rotated together around the second actuation rotation shaft 1131*b*. Here, the second actuation pulley 113P2 may include a single pulley or two pulleys fixedly coupled to each other.

Here, the first actuation gear 1134*a* and the second actuation gear 1134*b* may be engaged with each other, and thus if one of the first and second actuation gears 1134*a* and 1134*b* is rotated, the first and second actuation gears 1134*a* and 1134*b* may be rotated together in opposite directions.

The yaw manipulation part 112 may include a yaw rotation shaft 1121, a first jaw yaw pulley 112P1, a second jaw yaw pulley 112P2, and a yaw frame 1123. In addition, the yaw manipulation part 112 may further include a first jaw yaw auxiliary pulley 112S1 provided on a side of the first jaw yaw pulley 112P1, and a second jaw yaw auxiliary pulley 112S2 provided on a side of the second jaw yaw pulley 112P2. Here, the first jaw yaw auxiliary pulley 112S1 and the second jaw yaw auxiliary pulley 112S2 may be coupled to a pitch frame 1113 (described later).

In the drawings, it is illustrated that the yaw manipulation part 112 includes the first jaw yaw pulley 112P1 and the second jaw yaw pulley 112P2, and each of the first jaw yaw pulley 112P1 and the second jaw yaw pulley 112P2 includes two pulleys facing each other and independently rotatable. However, the idea of the present disclosure is not limited thereto. That is, according to the configuration of the yaw manipulation part 112, the yaw manipulation part 112 may include one or more pulleys having the same diameter or different diameters.

Specifically, the yaw rotation shaft 1121 is provided on a side of the actuation manipulation part 113 above the first handle 114. In this case, the first handle 114 is rotatable around the yaw rotation shaft 1121.

Here, the yaw rotation shaft 1121 may make a predetermined angle with the XY plane in which the connecting part 140 is provided. For example, the yaw rotation shaft 1121 may be oriented in a direction parallel to the Z axis, and in this state, if the pitch manipulation part 111 is rotated, the coordinate system of the yaw rotation shaft 1121 may be relatively varied as described above. However, the idea of the present disclosure is not limited thereto, and the yaw rotation shaft 1121 may be oriented in various directions according to ergonomic designs for the hand structure of a user holding the manipulation part 110.

In addition, the first jaw yaw pulley 112P1 and the second jaw yaw pulley 112P2 are coupled to the yaw rotation shaft 1121 such that the first jaw yaw pulley 112P1 and the second jaw yaw pulley 112P2 may be rotated on the yaw rotation shaft 1121. In addition, the first jaw wire 130J1 may be wound around the first jaw yaw pulley 112P1, and the second jaw wire 130J2 may be wound around the second jaw yaw pulley 112P2. In this case, each of the first jaw yaw pulley 112P1 and the second jaw yaw pulley 112P2 may include two pulleys facing each other and independently rotatable. Therefore, an inward wire and an outward wire may be respectively wound around separate pulleys and thus may not interfere with each other.

The yaw frame 1123 connects the first handle 114, the yaw rotation shaft 1121, the first actuation rotation shaft 1131*a*, and the second actuation rotation shaft 1131*b* such that the first handle 114, the yaw manipulation part 112, and the actuation manipulation part 113 may be rotated together around the yaw rotation shaft 1121.

The pitch manipulation part 111 may include the pitch rotation shaft 1111, a first jaw pitch pulley-a 111P1*a*, a first jaw pitch pulley-b 111P1*b*, a second jaw pitch pulley-a 111P2*a*, a second jaw pitch pulley-b 111P2*b*, and the pitch frame 1113. In addition, the pitch manipulation part 111 may further include a first jaw pitch auxiliary pulley-a 111S1*a* provided at a side of the first jaw pitch pulley-a 111P1*a*, a first jaw pitch auxiliary pulley-b 111S1*b* provided at a side of the first jaw pitch pulley-b 111P1*b*, a second jaw pitch auxiliary pulley-a 111S2*a* provided at a side of the second jaw pitch pulley-a 111P2*a*, and a second jaw pitch auxiliary pulley-b 111S2*b* provided at a side of the second jaw pitch pulley-b 111P2*b*. The pitch manipulation part 111 is connected to a bent part 141 of a connecting part 140 through the pitch rotation shaft 1111.

In detail, the pitch frame 1113 serves as a base frame of the pitch manipulation part 111, and the yaw rotation shaft 1121 is rotatably coupled to an end portion of the pitch frame 1113. That is, the yaw frame 1123 is rotatable around the yaw rotation shaft 1121 with respect to the pitch frame 1113.

As described above, the yaw frame 1123 connects the first handle 114, the yaw rotation shaft 1121, the first actuation rotation shaft 1131*a*, and the second actuation rotation shaft 1131*b* to each other, and is also connected to the pitch frame 1113. Therefore, if the pitch frame 1113 is rotated around the pitch rotation shaft 1111, the yaw frame 1123, the first handle 114, the yaw rotation shaft 1121, the first actuation rotation shaft 1131*a*, and the second actuation rotation shaft 1131*b* connected to the pitch frame 1113 are rotated together. That is, if the pitch manipulation part 111 is rotated around the pitch rotation shafts 1111, the actuation manipulation part 113 and the yaw manipulation part 112 are rotated together with the pitch manipulation part 111. In other words, if a user rotates the first handle 114 around the pitch rotation shaft 1111, the actuation manipulation part 113, the yaw manipulation part 112, and the pitch manipulation part 111 are moved together.

The pitch manipulation part 111, the first jaw pitch pulley-a 111P1*a*, the first jaw pitch pulley-b 111P1*b*, the second jaw pitch pulley-a 111P2*a*, and the second jaw pitch pulley-b 111P2*b* are coupled to the pitch frame 1113. In this case, the first jaw pitch pulley-a 111P1*a*, the first jaw pitch pulley-b 111P1b, the second jaw pitch pulley-a 111P2a, and the second jaw pitch pulley-b 111P2b are coupled to the pitch rotation shaft 1111 in a manner rotatable around the pitch rotation shaft 1111.

Here, the first jaw pitch pulley-a 111P1a and the first jaw pitch pulley-b 111P1b may face each other and may be independently rotated. Therefore, an inward wire and an outward wire may be respectively wound around separate pulleys and thus may not interfere with each other. Similarly, the second jaw pitch pulley-a 111P2a and the second jaw pitch pulley-b 111P2b may face each other and may be independently rotated. Therefore, an inward wire and an outward wire may be respectively wound around separate pulleys and thus may not interfere with each other.

Referring to FIG. 7, the pitch wire end pulley 115P is fixedly coupled to the pitch frame 1113 and rotatable together with the pitch frame 1113. In addition, the pitch wire 130P is fixedly coupled to the pitch frame 1113 through a pitch wire auxiliary pulley 115S and the pitch wire end pulley 115P. As a result, the pitch frame 1113 and the pitch wire end pulley 115P may be rotated together around the pitch rotation shaft 1111 by pitch rotation.

The pitch wire 130P is operated as follows.

The pitch pulley 123P is fixedly coupled to the end tool hub 123 of the end tool 120, and the manipulation part 110 includes the pitch wire end pulley 115P, wherein the pitch pulley 123P and the pitch wire end pulley 115P are connected to each other through the pitch wire 130P such that pitch motion of the end tool 120 may be easily performed by pitch-manipulating the manipulation part 110. Here, both ends of the pitch wire 130P are fixedly coupled to the pitch frame 1113 respectively through the pitch wire auxiliary pulley 115S and the pitch wire end pulley 115P, and the pitch wire end pulley 115P is also fixedly coupled to the pitch frame 1113. That is, the pitch frame 1113 and the pitch wire end pulley 115P are rotated together about the pitch rotation shaft 1111 by pitch rotation of the manipulation part, and as a result, both sides of the pitch wire 130P are also moved in opposite directions such that additional power for pitch rotation may be transmitted independently of pitch motion of the end tool by the first jaw wire 130J1 and the second jaw wire 130J2.

The first handle 114, the pitch manipulation part 111, the yaw manipulation part 112, and the actuation manipulation part 113 are connected as follows. The actuation rotation shafts 1131a and 1131b, the yaw rotation shaft 1121, and the pitch rotation shaft 1111 may be provided on the first handle 114. In this case, since the actuation rotation shafts 1131a and 1131b are directly provided on the first handle 114, and the first handle 114 and the actuation manipulation part 113 may be directly connected to each other. In addition, since the yaw rotation shaft 1121 is directly provided on the first handle 114, the first handle 114 and the yaw manipulation part 112 may be directly connected to each other. However, since the pitch manipulation part 111 is provided at a side of the yaw manipulation part 112 and connected to the yaw manipulation part 112, the pitch manipulation part 111 may not be directly connected to the first handle 114 but may be indirectly connected to the first handle 114 through the yaw manipulation part 112.

Referring to the drawings, in the instrument 100 for surgery according to the first embodiment of the present disclosure, the pitch manipulation part 111 and the end tool 120 may be provided on the same axis or on parallel axes (to the X axis). That is, the pitch rotation shaft 1111 of the pitch manipulation part 111 is provided on an end portion of the bent part 141 of the connecting part 140, and the end tool 120 is provided on the other end portion of the connecting part 140.

In addition, one or more relay pulleys MP may be placed on a middle portion of the connecting part 140, particularly, on the bent part 141 of the connecting part 140 to change paths of wires or guide wires. At least portions of wires may be wound around the relay pulleys MP, thereby guiding paths of the wires and arranging the wires along a bent shape of the bent part 141.

In the drawings, it is illustrated that the connecting part 140 includes the bent part 141 and has a curved shape with a predetermined radius of curvature. However, the idea of the present disclosure is not limited thereto. If necessary, the connecting part 140 may have a straight shape or may be bent at least one time, and even in this case, it may be stated that the pitch manipulation part 111 and the end tool 120 are provided substantially on the same axis or parallel axes. In addition, although FIG. 3 illustrates that the pitch manipulation part 111 and the end tool 120 are provided on an axis parallel to the X axis, the idea of the present disclosure is not limited thereto. For example, the pitch manipulation part 111 and the end tool 120 may be provided on different axes.

Actuation Motion, Yaw Motion, Pitch Motion

Actuation motion, yaw motion, and pitch motion in this embodiment will be described as follows.

First, the actuation motion is as follows.

When a user rotates actuation rotating portions 1132a and 1132b using one or both of an index finger inserted into a hand ring 150 connected to a first actuation rotating portion 1132a and a thumb inserted into a hand ring 150 connected to a second actuation rotating portion 1132b, a first actuation pulley 113P1 fixedly coupled to the first actuation rotating portion 1132a and a first actuation gear 1134a are rotated around a first actuation rotation shaft 1131a, and a second actuation pulley 113P2 fixedly coupled to the second actuation rotating portion 1132b and a second actuation gear 1134b are rotated around a second actuation rotation shaft 1131b. At this time, as the first actuation pulley 113P1 and the second actuation pulley 113P2 rotate in opposite directions, a first jaw wire 130J1 having one end fixedly coupled to and wound on the first actuation pulley 113P1 and a second jaw wire 130J2 having one end fixedly coupled to and wound on the second actuation pulley 113P2 also move in opposite directions. And, this rotational force is transmitted to an end tool 120 through a power transmission portion 130, two jaws 121 and 122 of the end tool 120 perform the actuation motion.

Here, the actuation motion refers to an action of opening or closing the jaws 121 and 122 while the two jaws 121 and 122 rotate in opposite directions to each other, as described above. That is, when the actuation rotating portions 1132a and 1132b of an actuation manipulation portion 113 are rotated in a direction closer to each other, a first jaw 121 rotates counterclockwise and a second jaw 122 rotates clockwise to close the end tool 120, but when the actuation rotating portions 1132a and 1132b of the actuation manipulation portion 113 are rotated in a direction away from each other, the first jaw 121 rotates clockwise and the second jaw 122 rotates counterclockwise to open the end tool 120. In this embodiment, for the above-described actuation manipulation, the first actuation rotating portion 1132a and the second actuation rotating portion 1132b were provided to constitute a second handle, and two fingers were gripped to enable manipulation. However, unlike the above, the actuation manipulation portion 113 for actuation manipulation to open and close the two jaws of the end tool 120 with each other may be configured differently so that, for example, two actuation pulleys (first actuation pulley 113P1, second actuation pulley 113P2) operate opposite to each other by one actuation rotating portion.

Next, the yaw motion is as follows.

When the user rotates a first handle 114 around a yaw rotation shaft 1121 while holding the first handle 114, the actuation manipulation portion 113 and a yaw manipulation portion 112 make yaw rotation around the yaw rotation shaft 1121. That is, when the first actuation pulley 113P1 of a first actuation manipulation portion 113a fixedly coupled to the first jaw wire 130J1 rotates around the yaw rotation shaft 1121, the first jaw wire 130J1 wound on a first jaw yaw pulley 112P1 moves. Similarly, when the second actuation pulley 113P2 of a second actuation manipulation portion 113b fixedly coupled to the second jaw wire 130J2 rotates around the yaw rotation shaft 1121, the second jaw wire 130J2 wound around a second jaw yaw pulley 112P2 moves. At this time, the first jaw wire 130J1 connected to the first jaw 121 and the second jaw wire 130J2 connected to the second jaw 122 are wound around the first jaw yaw pulley 112P1 and the second jaw yaw pulley 112P2, so that the first jaw 121 and the second jaw 122 rotate in the same direction during yaw rotation. And, this rotational force is transmitted to the end tool 120 through the power transmission portion 130, the two jaws 121 and 122 of the end tool 120 performs the yaw motion that rotates in the same direction.

At this time, since a yaw frame 1123 connects the first handle 114, yaw rotation shaft 1121, first actuation rotation shaft 1131a and second actuation rotation shaft 1131b, first handle 114, yaw manipulation portion 112 and actuation manipulation portion 113 are rotated together around the yaw rotation shaft 1121.

Next, the pitch motion is as follows.

When the user rotates the first handle 114 around a pitch rotation shaft 1111 while holding the first handle 114, the actuation manipulation portion 113, the yaw manipulation portion 112 and a pitch manipulation portion 111 make pitch rotation around the pitch rotation shaft 1111. That is, when the first actuation pulley 113P1 of the first actuation manipulation portion 113a fixedly coupled to the first jaw wire 130J1 rotates around the pitch rotation shaft 1111, the first jaw wire 130J1 wound on a first jaw pitch pulley-a 111P1a and a first jaw pitch pulley-b 111P1b moves. Similarly, when the second actuation pulley 113P2 of the second actuation manipulation portion 113b fixedly coupled to the second jaw wire 130J2 rotates around the pitch rotation shaft 1111, the second jaw wire 130J2 wound on a second jaw pitch pulley-a 111P2a and a second jaw pitch pulley-b 111P2b moves. At this time, the first jaw wire 130J1 and the second jaw wire 130J2 are wound on a first jaw pitch pulley 111P1a, 111P1b and a second jaw pitch pulley 111P2a, 111P2b, so that, as described through FIG. 5, both strands of the first jaw wire 130J1 move in the same direction, and both strands of the second jaw wire 130J2 move in the same direction, thus the first jaw 121 and second jaw 122 may perform pitch rotation. And, this rotational force is transmitted to the end tool 120 through the power transmission portion 130, so that the two jaws 121 and 122 of the end tool 120 performs a pitch motion.

At this time, when a pitch frame 1113 rotates around the pitch rotation shaft 1111, the yaw frame 1123 connected to the pitch frame 1113, first handle 114, yaw rotation shaft 1121, first actuation rotation shaft 1131a and second actuation rotation shaft 1131b rotate together because the pitch frame 1113 is connected to the yaw frame 1123, and the yaw frame 1123 connects the first handle 114, the yaw rotation shaft 1121, the first actuation rotation shaft 1131a and the second actuation rotation shaft 1131b. That is, when the pitch manipulation portion 111 rotates around the pitch rotation shaft 1111, the actuation manipulation portion 113 and the yaw manipulation portion 112 are rotated together with the pitch manipulation portion 111.

In summary, in a surgical instrument 100 according to an embodiment of the present disclosure, it is characterized that pulleys are formed at each joint point (actuation joint, yaw joint, pitch joint), wire (first jaw wire or second jaw wire) is wound on the pulley, and rotational manipulation of the manipulation portion (actuation rotation, yaw rotation, pitch rotation) causes movement of each wire, as a result, a desired motion of the end tool 120 is induced. Furthermore, auxiliary pulleys may be formed on one side of each pulley, and the wire may not be wound several times on one pulley by these auxiliary pulleys.

Accordingly, as illustrated in FIG. 7 illustrating a first embodiment, the actuation operation, the yaw operation, and the pitch operation may be performed independently of each other.

As described through FIG. 1, the actuation manipulation portion 113, yaw manipulation portion 112, and pitch manipulation portion 111 have their own rotation shafts located at the back of each manipulation portion, so it is configured the same as the joint configuration of the end tool, allowing the user to perform intuitively matching operations.

Especially, in a surgical instrument 100 according to an embodiment of the present disclosure, it is characterized that pulleys are formed at each joint point (actuation joint, yaw joint, pitch joint), wire (first jaw wire or second jaw wire) is wound on the pulley, and rotational manipulation of the manipulation portion (actuation rotation, yaw rotation, pitch rotation) causes movement of each wire, as a result, a desired motion of the end tool 120 is induced. Furthermore, auxiliary pulleys may be formed on one side of each pulley, and the wire may not be wound several times on one pulley by these auxiliary pulleys, so that the wires wound on the pulley do not come into contact with each other, and the path of the wire that goes into the pulley and the wire that comes out is also formed safely, so the safety and efficiency of power transmission of the wire may be improved.

On the other hand, as described above, the yaw manipulation portion 112 and the actuation manipulation portion 113 are formed directly on the first handle 114. Therefore, when the first handle 114 rotates around the pitch rotation shaft 1111, the yaw manipulation portion 112 and the actuation manipulation portion 113 also rotate together with the first handle 114. Due to this, a coordinate system of the yaw manipulation portion 112 and the actuation manipulation portion 113 is not fixed, but continues to change relatively according to the rotation of the first handle 114. That is, in FIG. 2 and the like, the yaw manipulation portion 112 and the actuation manipulation portion 113 are illustrated as being parallel to a Z-axis. However, when the first handle 114 is rotated, the yaw manipulation portion 112 and the actuation manipulation portion 113 are not parallel to the Z-axis. That is, the coordinate system of the yaw manipulation portion 112 and the actuation manipulation portion 113 is changed according to the rotation of the first handle 114. However, in the present specification, for convenience of explanation, if there is no separate explanation, the coordinate system of the yaw manipulation portion 112 and the actuation manipulation portion 113 was described based on a state in which the first handle 114 is positioned vertically with respect to the connection portion 140 as illustrated in FIG. 2.

Pin Assembly

Figure 9:
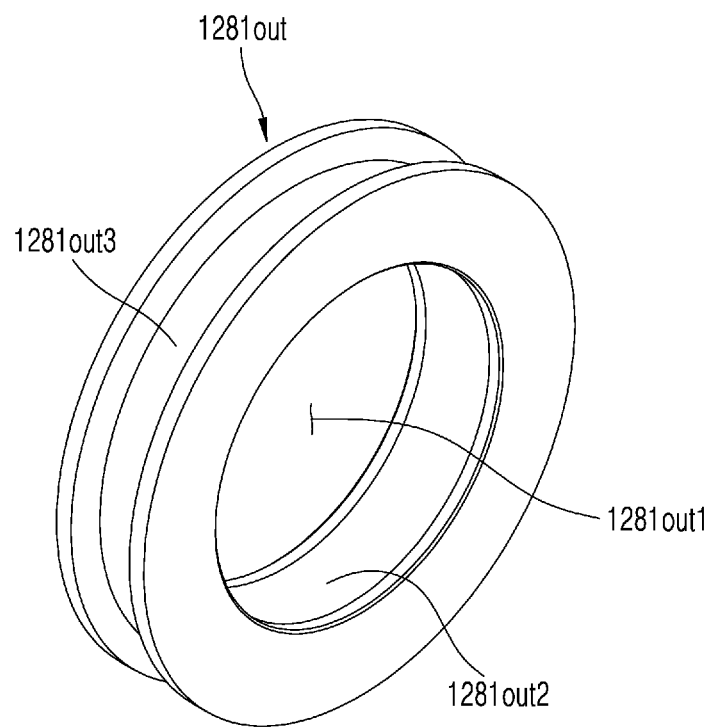
FIG. 9 is a perspective view of a fourth pin first outer pulley of the end tool for the surgical instrument of FIG. 2.
Figure 10:
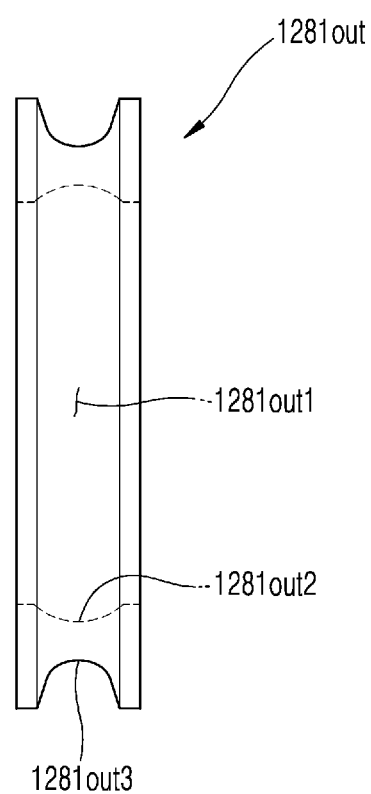
FIG. 10 is a side view of the fourth pin first outer pulley of FIG. 9.
Figure 11:
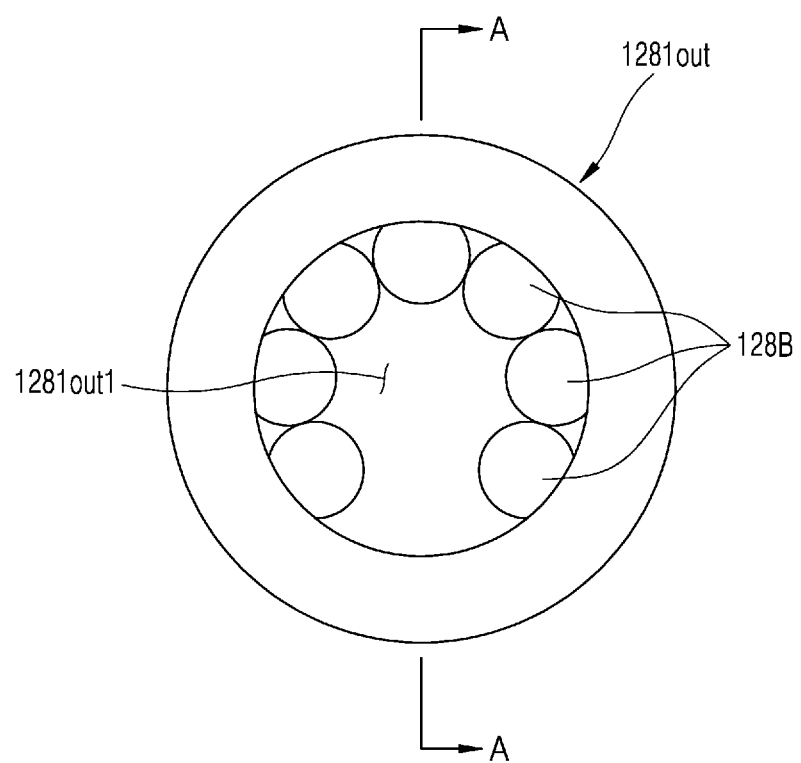
FIG. 11 is a plan view showing a state in which friction reducing members arranged on the fourth pin first outer pulley of FIG. 9.
Figure 12:
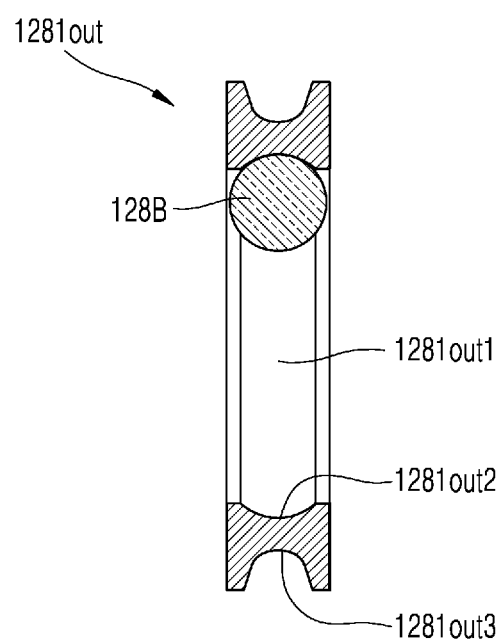
FIG. 12 is a cross-sectional view taken along a line A-A of FIG. 11.
Figure 13:
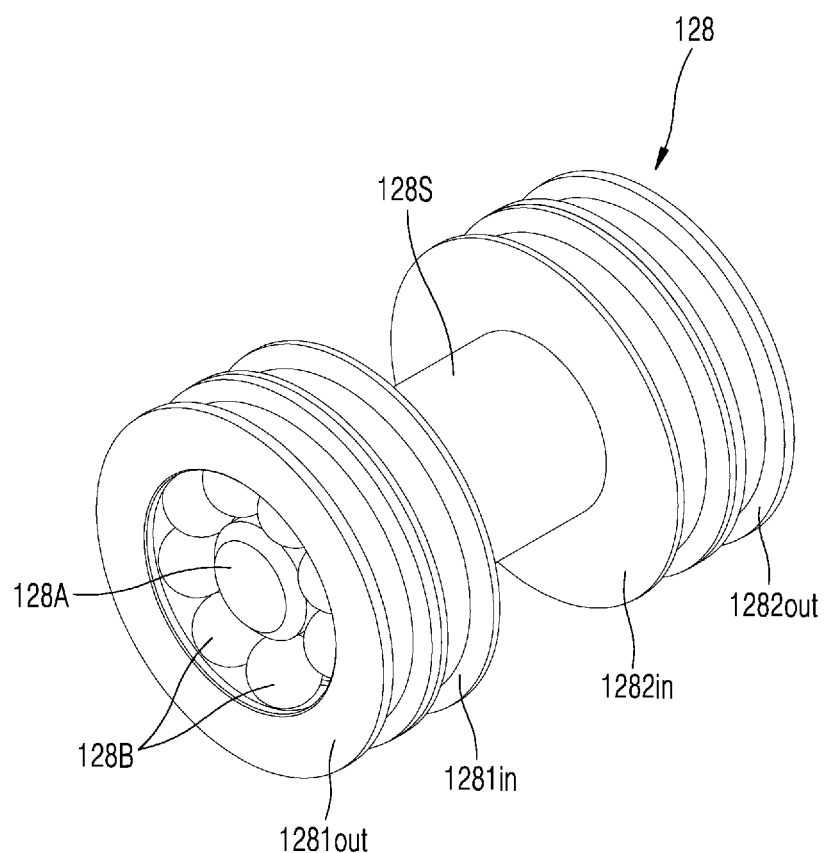
FIG. 13 is a perspective view of a fourth pin assembly in the end tool for the surgical instrument of FIG. 2.
Figure 14:
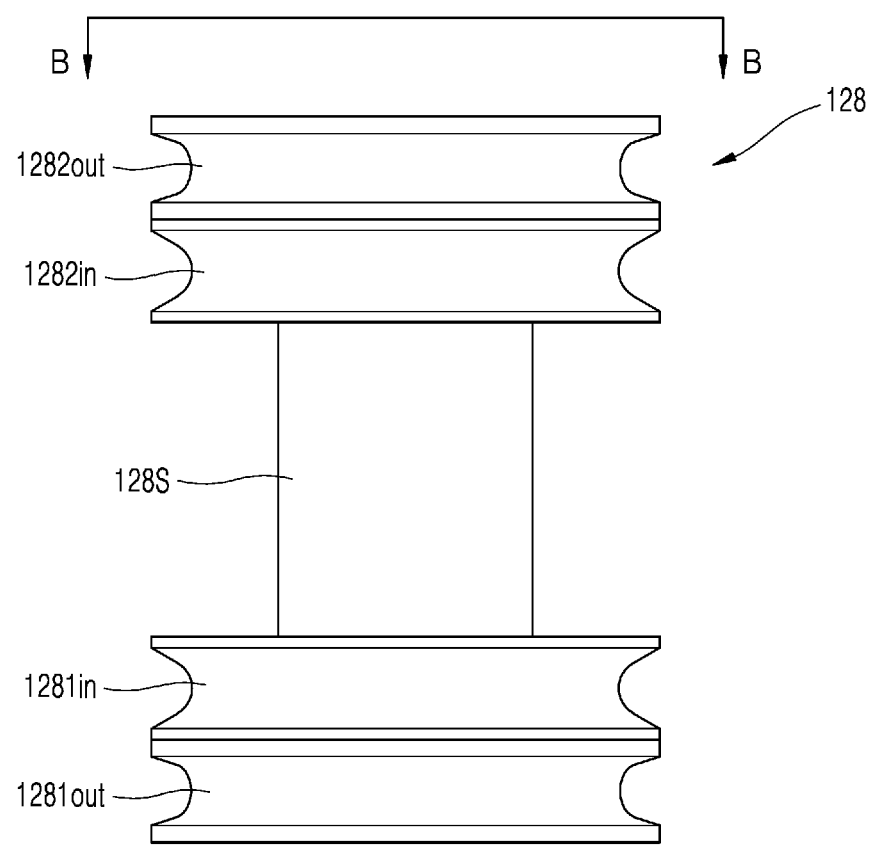
FIG. 14 is a front view of the fourth pin assembly of FIG. 13.
Figure 15:
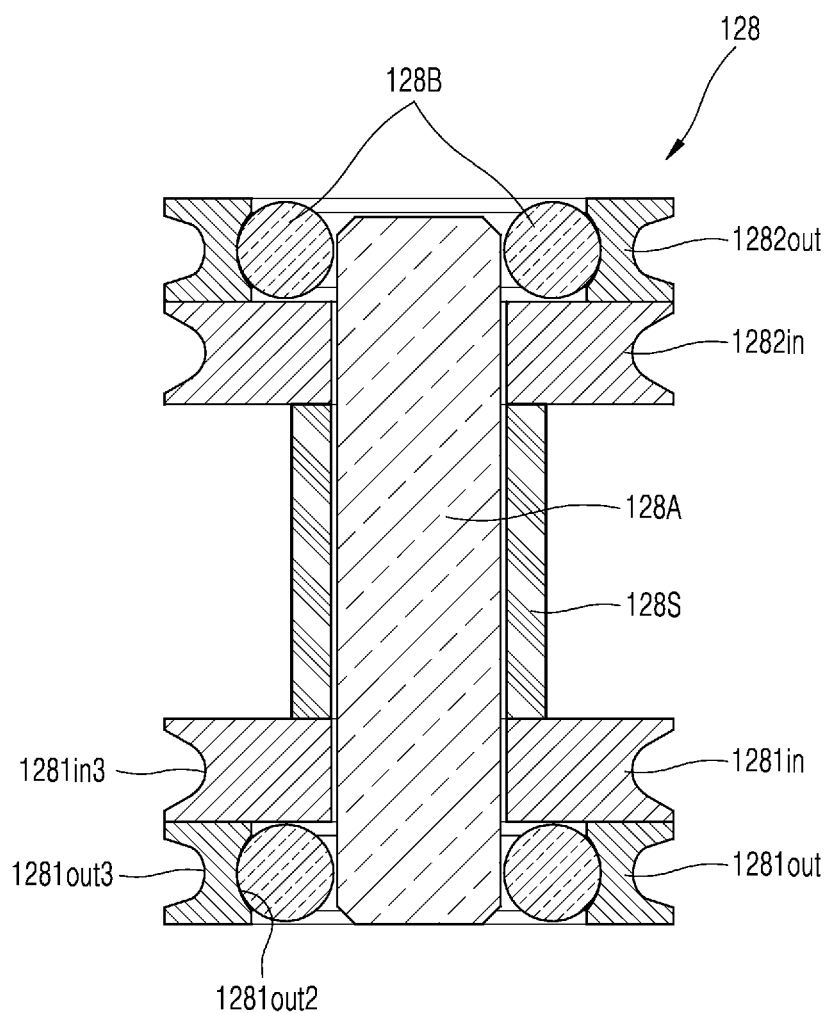
FIG. 15 is a cross-sectional view taken along line B-B of FIG. 14.

FIG. 9 is a perspective view of a fourth pin first outer pulley 1281out of an end tool 120 for a surgical instrument of FIG. 2, and FIG. 10 is a side view of the fourth pin first outer pulley 1281out of FIG. 9. FIG. 11 is a plan view showing a state in which friction reducing members 128B arranged on the fourth pin first outer pulley 1281out of FIG. 9, and FIG. 12 is a cross-sectional view taken along line A-A of FIG. 11. FIG. 13 is a perspective view of a fourth pin assembly 128 in the end tool of the surgical instrument of FIG. 2, FIG. 14 is a front view of the fourth pin assembly 128 of FIG. 13, and FIG. 15 is a cross-sectional view taken along line B-B of FIG. 14.

The end tool 120 may include four pins that are rotating centers of respective pulleys, e.g., a first pin 125A, a second pin 126A, a third pin 127A, and a fourth pin 128A formed thereon, and may include four pin assemblies 125, 126, 127, and 128 respectively including the pins. Here, each of the pin assemblies may include a pin, e.g., the rotary shaft, and one or more pulleys rotating about the pin, and as necessary, may further include additional components such as a spacer, etc.

The first pin 125A serves as a yaw axis, the second pin 126A serves as a yaw auxiliary axis, the third pin 127A serves as a pitch main axis, and the fourth pin 128A serves as a pitch auxiliary axis. In addition, when a structure substituting for the pulley is formed in an end tool hub and the yaw auxiliary axis is not necessary, the second pin assembly may be omitted.

Hereinafter, descriptions will be provided based on the fourth pin assembly 128 below.

Referring to FIGS. 9 to 15, the fourth pin assembly 128 includes the fourth pin 128A, a fourth pin first outer pulley 1281out, a fourth pin first inner pulley 1281in, a fourth pin second outer pulley 1282out, a fourth pin second inner pulley 1282in, and a fourth pin spacer 128S.

Here, the fourth pin first outer pulley 1281out, the fourth pin first inner pulley 1281in, the fourth pin spacer 128S, the fourth pin second inner pulley 1282in, and the fourth pin second outer pulley 1282out may be sequentially fitted onto the fourth pin 128A therethrough.

Here, a plurality of friction reducing members 128B of ball shapes are additionally arranged between the pulley and the pin in the fourth pin first outer pulley 1281out and the fourth pin second outer pulley 1282out to which a strong force is applied, and function as ball bearings. In the present embodiment, balls are provided as the friction reducing members 128B. This will be described below in more detail.

The fourth pin first outer pulley 1281out is formed as a loop shape having a hollow portion 1281out1 formed therein, and may have a groove 1281out2, on which friction reducing members 128B that will be described later are mounted, in an inner circumferential surface thereof. In addition, a groove 1281out 3 on which a wire is to be wound may be also formed in an outer circumferential surface of the fourth pin first outer pulley 1281out.

Here, at least some parts of the plurality of friction reducing members 128B are accommodated in the groove 1281out2 formed in the inner circumferential surface of the fourth pin first outer pulley 1281out. When expressed from another point of view, the groove 1281out2 may prevent the friction reducing members 128B from escaping from the fourth pin first outer pulley 1281out. That is, the groove 1281out2 formed in the inner circumferential surface of the fourth pin first outer pulley 1281out may be formed to correspond to the diameters of the friction reducing members 128B, and a part of each of the friction reducing members 128B is inserted in the groove 1281out2, and thus, the friction reducing members 128B may not be removed out of the fourth pin first outer pulley 1281out and remain in the original places.

Here, in order to insert the friction reducing members 128B in the groove 1281out2, the diameter of the groove 1281out2 and the diameter of each of the friction reducing members 128B may be substantially equal to each other, or the diameter of the groove 1281out2 may be slightly greater than that of each friction reducing member 128B.

Here, the plurality of friction reducing members 128B are arranged in the hollow portion 1281out1 of the fourth pin first outer pulley 1281out, and the fourth pin 128A is inserted into a central area among the friction reducing members 128B. Therefore, instead of direct contact between the fourth pin 128A and the fourth pin first outer pulley 1281out, the fourth pin 128A is in direct contact with the friction reducing members 128B. To do this, a diameter of the hollow portion 1281out1 of the fourth pin first outer pulley 1281out may be greater than that of the fourth pin 128A by a certain degree.

As described above, the fourth pin assembly 128 of the present disclosure is basically similar to the ball bearing, but without forming an additional inner wheel, the friction reducing members 128B and the outer circumferential surface of the fourth pin 128A (rotary shaft) are in direct contact with each other. In other words, the fourth pin first outer pulley 1281out and the fourth pin 128A are not in direct contact with each other, but the friction reducing members 128B are interposed such that the friction reducing members 128B are in contact with the fourth pin 128A, and thus, the force and friction applied to the pulley and the pin may be distributed in order to implement soft movements, and at the same time, a probability of breakage may be reduced.

In addition, the fourth pin first inner pulley 1281in is formed as a loop shape having a hollow portion (see 1281in 1 of FIG. 19) formed therein. Here, the fourth pin first inner pulley 1281in may be a raw pulley that does not have a groove formed in an inner circumferential surface thereof. In addition, a groove 1281in 3 for winding a wire may be also formed on an outer circumferential surface of the fourth pin first inner pulley 1281in. Here, an additional ball may not be disposed between the fourth pin first inner pulley 1281in and the fourth pin 128A. Therefore, the fourth pin first inner pulley 1281in and the fourth pin 128A may be in direct contact with each other. To this end, a diameter of the hollow portion of the fourth pin first inner pulley 1281in may be substantially equal to or slightly greater than that of the fourth pin 128A.

A spacer 128S is disposed between the fourth pin first inner pulley 1281in and the fourth pin second inner pulley 1282in, and supports the fourth pin first inner pulley 1281in and the fourth pin second inner pulley 1282in to maintain a constant gap therebetween. Here, because the spacer 128S is directly fitted onto the fourth pin 128A, an inner diameter of the spacer 128S may be substantially equal to or slightly greater than the diameter of the fourth pin 128A.

The fourth pin second inner pulley 1282in is formed to be substantially the same as the fourth pin first inner pulley 1281in, and the fourth pin second outer pulley 1282out may be formed to be substantially the same as the fourth pin first outer pulley 1281out.

The present disclosure as described above may be seen as an intermediate form between a structure in which a shaft is simply inserted in a pulley and a structure in which a shaft is inserted in a ball bearing. That is, a general ball bearing has an inner ring and an outer ring, but in the present disclosure, the pulley serves as a kind of outer ring of the bearing. In addition, although balls are disposed inside the ball bearing, an additional inner ring is not provided, and the shaft is in direct contact with the ball. In addition, in order to prevent the ball from being removed, a groove having a size/shape corresponding to the diameter of the ball is formed in the inner circumferential surface of the pulley.

According to the present disclosure as described above, a plurality of balls are arranged between the pulley and the pin (rotary shaft) similarly to the ball bearing, such that the load applied to the pin (rotary shaft) and the pulley is appropriately distributed. Thus, the pulley may be smoothly rotated, and at the same time, an overall durability may be improved. In addition, because a separate inner ring is not provided, the number of components and manufacturing cost are reduced, and moreover, there may be an effect of saving an inner space corresponding to the width of the inner ring.

In addition, the third pin assembly 127 includes the third pin 127A, a third pin first outer pulley 1271out, a third pin first inner pulley 1271in, a third pin second outer pulley 1272out, and a third pin second inner pulley 1272in.

Here, the third pin first outer pulley 1271out, the third pin first inner pulley 1271in, a pitch pulley 123P/the end tool hub 123, the third pin second inner pulley 1272in, and the third pin second outer pulley 1272out may be sequentially fitted onto the third pin 127A therethrough.

That is, the third pin assembly 127 is the same as the fourth pin assembly 128 except that the pitch pulley 123P and the end tool hub 123, instead of the spacer 128S, are fitted therein.

Also, although the pitch pulley 123P and the end tool hub 123 are shown as separate members in the drawings, but the present disclosure is not limited thereto, that is, a groove may be formed in the end tool hub 123 such that the pitch wire is wound thereon, and thus, the end tool hub 123 may also function as the pitch pulley.

In addition, like the fourth pin assembly 128, a plurality of balls are additionally arranged between the pulley and the pin in the third pin first outer pulley 1271out and the third pin second outer pulley 1272out to function as the ball bearing.

The second pin assembly 126 includes the second pin 126A, a second pin first jaw pulley 1261, a second pin second jaw pulley 1262, and a second pin spacer 126S. Here, the second pin first jaw pulley 1261, the second pin spacer 126S, and the second pin second jaw pulley 1262 may be sequentially fitted onto the second pin 126A therethrough.

The first pin assembly 125 includes the first pin 125A, a first pin first jaw pulley 1251, and a first pin second jaw pulley 1252. Here, the first pin first jaw pulley 1251 and the first pin second jaw pulley 1252 may be sequentially fitted onto the first pin 125A therethrough. The first jaw 121 may be coupled to the first pin first jaw pulley 1251 and the second jaw 122 may be coupled to the first pin second jaw pulley 1252.

Method of Manufacturing a Pin Assembly

A method of manufacturing the fourth pin assembly 128 will be described below.

FIGS. 16 to 26 are diagrams illustrating a method of manufacturing the fourth pin assembly 128. Each of the drawings below shows a plan view and a side view together.

Figure 16:
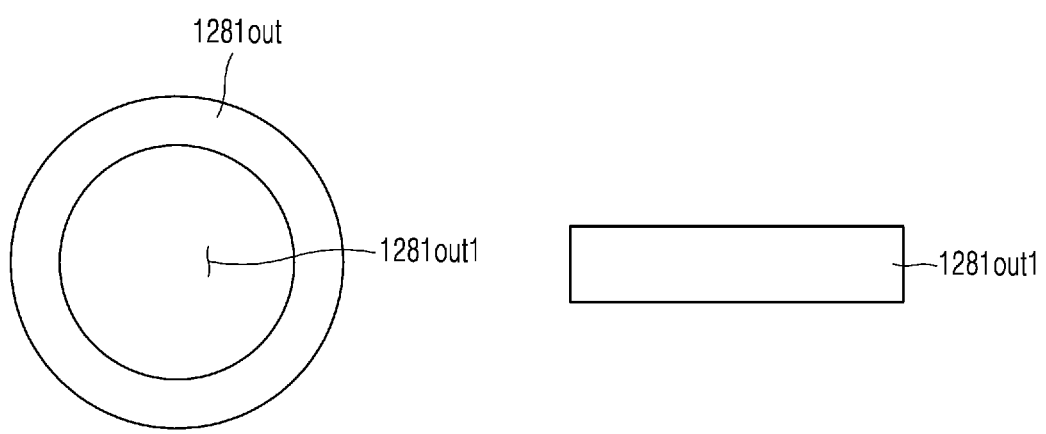
FIGS. 16 to 26 are diagrams illustrating a method of manufacturing a fourth pin assembly.

First, as shown in FIG. 16, the fourth pin first outer pulley 1281out is arranged on a plane. Here, as described above, the hollow portion 1281out1 and the groove (see 1281out2 of FIG. 9) may be formed in the fourth pin first outer pulley 1281out.

Figure 17:
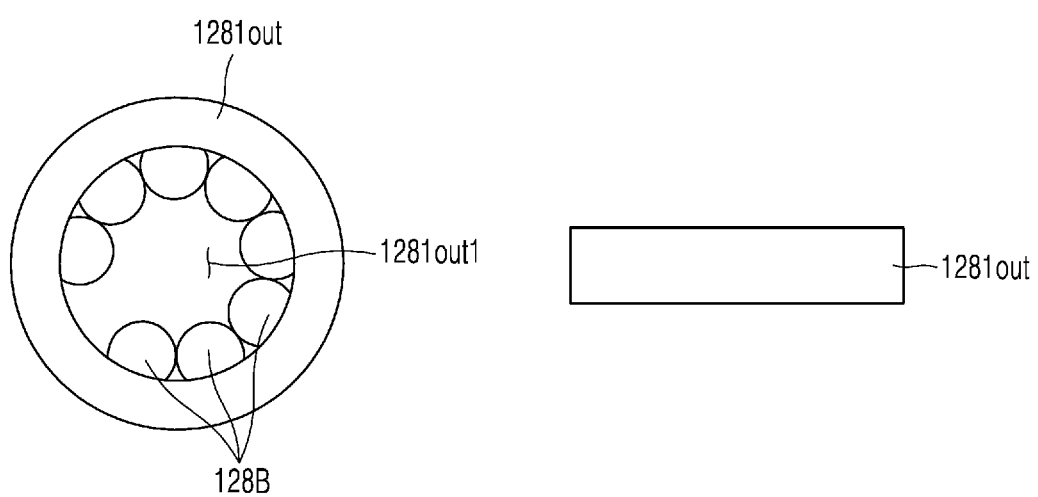

Next, as shown in FIG. 17, a plurality of friction reducing members 128B are arranged in the hollow portion 1281out1 of the fourth pin first outer pulley 1281out. Although FIG. 17 shows that eight balls are arranged, the present disclosure is not limited thereto. That is, the number of the friction reducing members 128B may vary according to the sizes and shapes of the fourth pin first outer pulley 1281out and the friction reducing members 128B.

Figure 18:
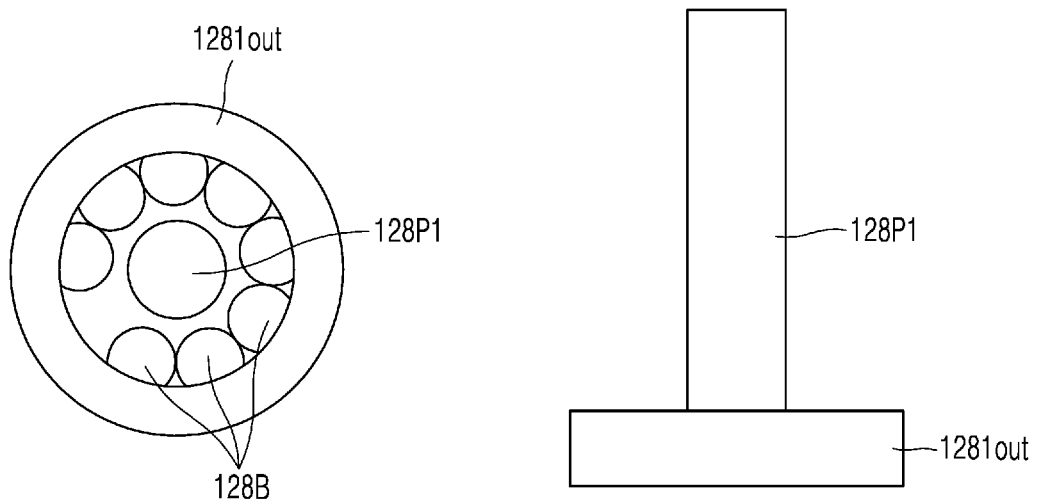

Next, as shown in FIG. 18, a first replacement pin 128P1 is inserted among the friction reducing members 128B. In order to facilitate the insertion of the first replacement pin 128P1 among the friction reducing members 128B, the first replacement pin 128P1 may have a slightly less diameter than that of the fourth pin (see 128A of FIG. 15) to be inserted later. Here, as the first replacement pin 128P1 is inserted, the friction reducing members 128B are pushed toward the groove (see 1281ou2 of FIG. 9) in the inner circumferential surface of the fourth pin first outer pulley 1281out, and thus, each of the friction reducing members 128B may be closely coupled to the groove (see 1281out2 of FIG. 9) of the fourth pin first outer pulley 1281out. Because each of the friction reducing members 128B comes into a close contact with the groove (see 1281out2 of FIG. 9) as described above, the friction reducing members 128B may be prevented from being removed out of the fourth pin first outer pulley 1281out.

Figure 19:
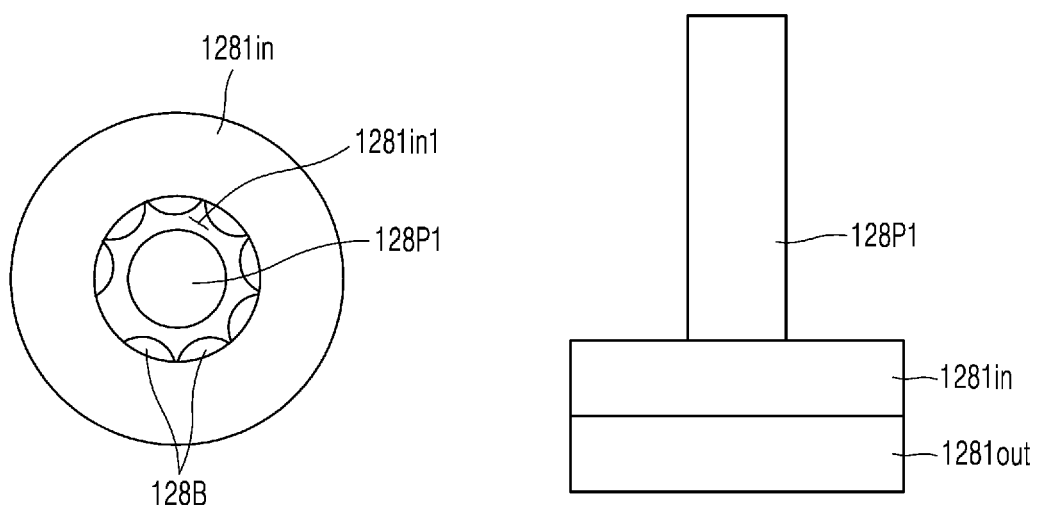

Next, as shown in FIG. 19, the fourth pin first inner pulley 1281in is fitted onto the first replacement pin 128P1 such that the fourth pin first inner pulley 1281in is stacked on the fourth pin first outer pulley 1281out. Here, the fourth pin first inner pulley 1281in and the fourth pin second inner pulley 1282in that will be described later may include raw pulleys in which grooves are not formed in the inner circumferential surfaces thereof. Therefore, the fourth pin first inner pulley 1281in and the fourth pin second inner pulley 1282in may be formed to be in direct contact with the fourth pin (see 128A of FIG. 15) after the assembly is finished.

Figure 20:
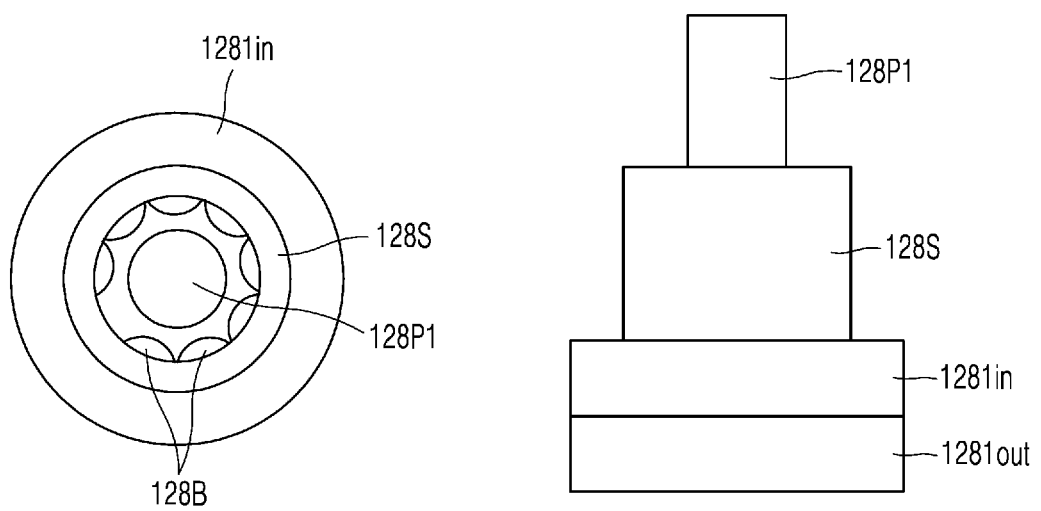

Next, as shown in FIG. 20, the fourth pin spacer 128S is fitted onto the first replacement pin 128P1 such that the fourth pin spacer 128S may be stacked on the fourth pin first inner pulley 1281in. The fourth pin spacer 128S supports the fourth pin first inner pulley 1281in and the fourth pin second inner pulley 1282in so as to maintain a certain gap between the fourth pin first inner pulley 1281in and the fourth pin second inner pulley 1282in.

Figure 21:
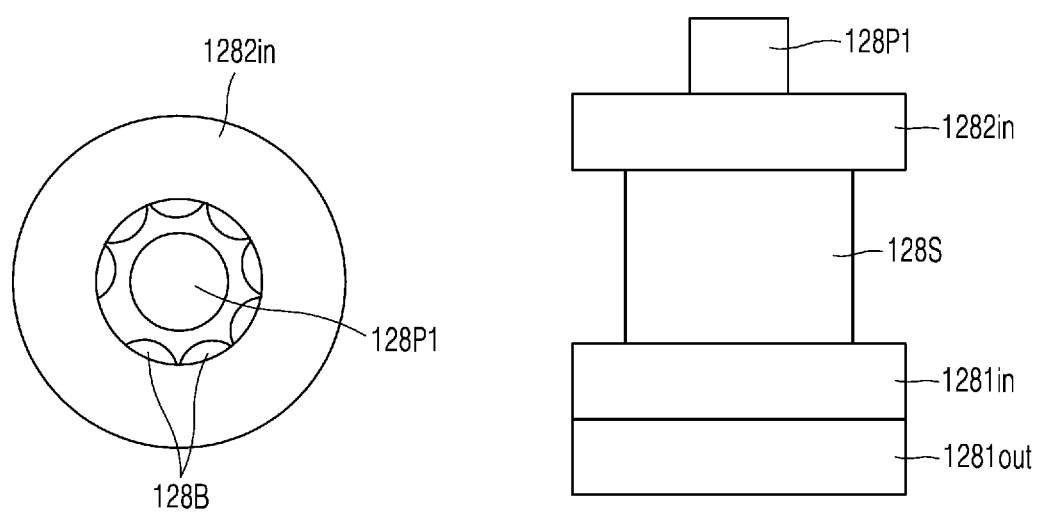

Next, as shown in FIG. 21, the fourth pin second inner pulley 1282in is fitted onto the first replacement pin 128P1 such that the fourth pin second inner pulley 1282in is stacked on the fourth pin spacer 128S.

Figure 22:
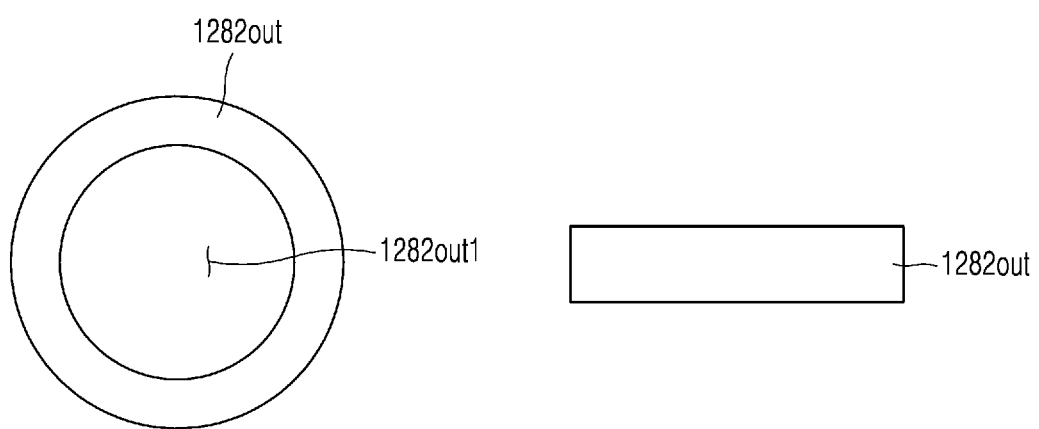

Next, as shown in FIG. 22, the fourth pin second outer pulley 1282out is arranged on a plane. Here, as described above, the hollow portion 1282out 1 and the groove (see 1281out2 of FIG. 9) may be formed in the fourth pin second outer pulley 1282out.

Figure 23:
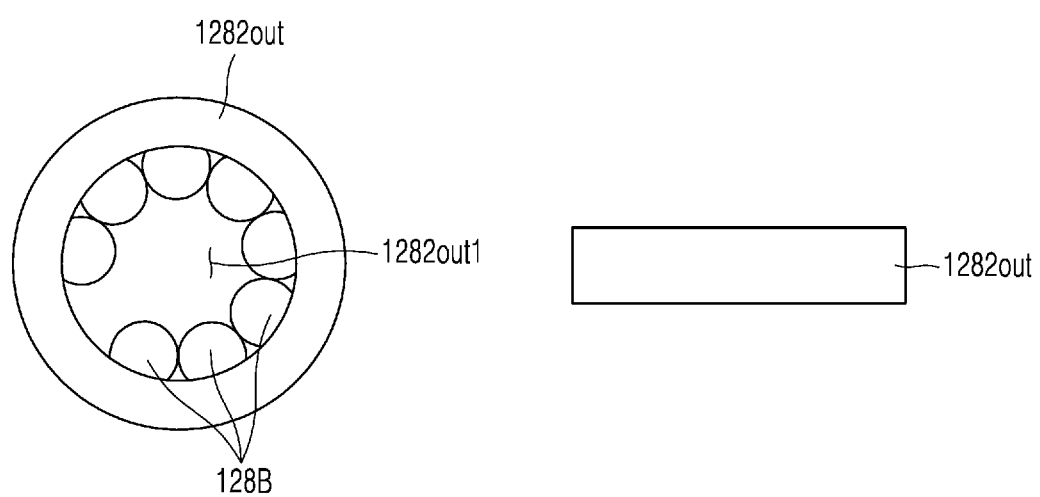

Next, as shown in FIG. 23, the plurality of friction reducing members 128B are arranged in the hollow portion 1282out 1 of the fourth pin second outer pulley 1282out.

Figure 24:
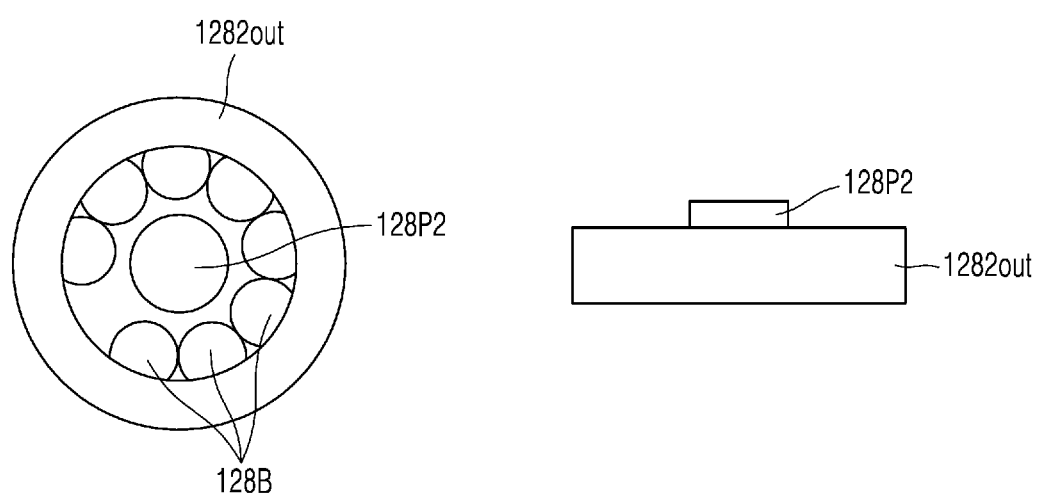

Next, as shown in FIG. 24, a second replacement pin 128P2 is inserted among the friction reducing members 128B. In order to facilitate the insertion of the second replacement pin 128P2 among the friction reducing members 128B, the second replacement pin 128P2 may have a slightly less diameter than that of the fourth pin (see 128A of FIG. 15) that will be inserted later. Here, as the second replacement pin 128P2 is inserted, the friction reducing members 128B are pushed toward the groove (see 1281*ou*2 of FIG. 9) of the fourth pin second outer pulley 1282*out*, and thus, each of the friction reducing members 128B may be closely coupled to the groove (see 1281*out*2 of FIG. 9) of the fourth pin second outer pulley 1282*out*. Because each of the friction reducing members 128B is in close contact with the groove (see 1281*out*2 of FIG. 9) as described above, the friction reducing members 128B may be prevented from being removed out of the fourth pin second outer pulley 1282*out*.

Figure 25:
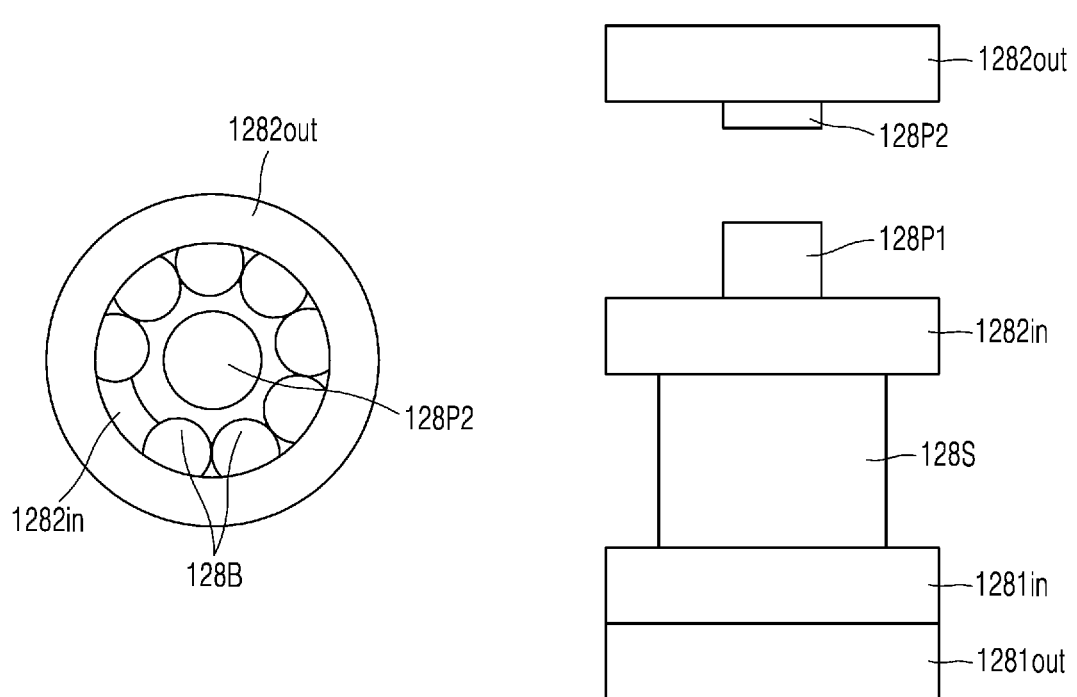
Figure 26:
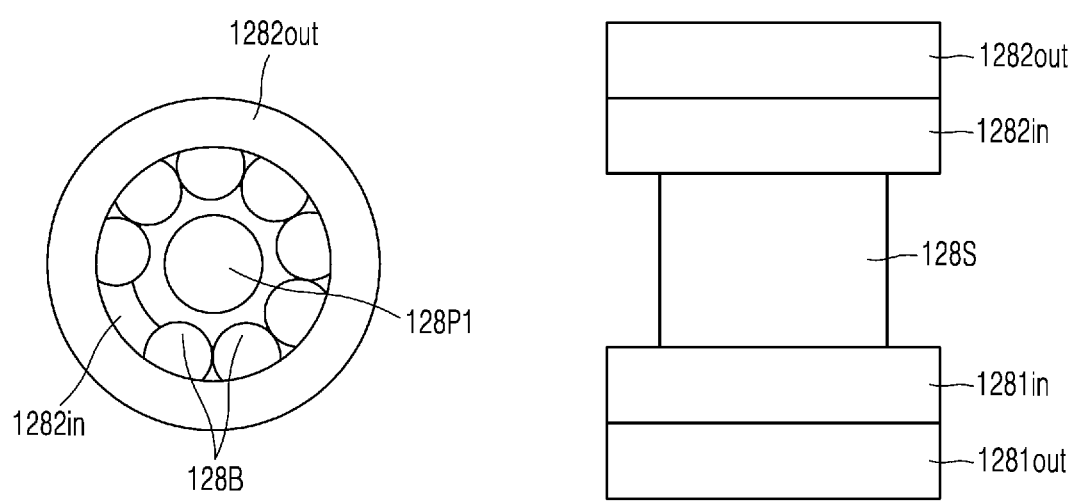

Next, as shown in FIG. 25, in a state in which the fourth pin second outer pulley 1282*out* and the friction reducing members 128B are fitted with the second replacement pin 128P2, the first replacement pin 128P1 is inserted in the fourth pin second outer pulley 1282*out* while pushing away the second replacement pin 128P2. Consequently, as shown in FIG. 26, the fourth pin second outer pulley 1282*out* and the friction reducing members 128B are transferred to be fitted onto the first replacement pin 128P1, and the fourth pin assembly 128 is primarily completed.

Next, a process of coupling the fourth pin assembly 128 to a pitch hub 124 will be described below.

FIGS. 27 to 31 are diagrams showing processes of coupling the fourth pin assembly 128 to the pitch hub 124. Here, the pitch hub 124 is shown abbreviated to the extent necessary for description.

Figure 27:
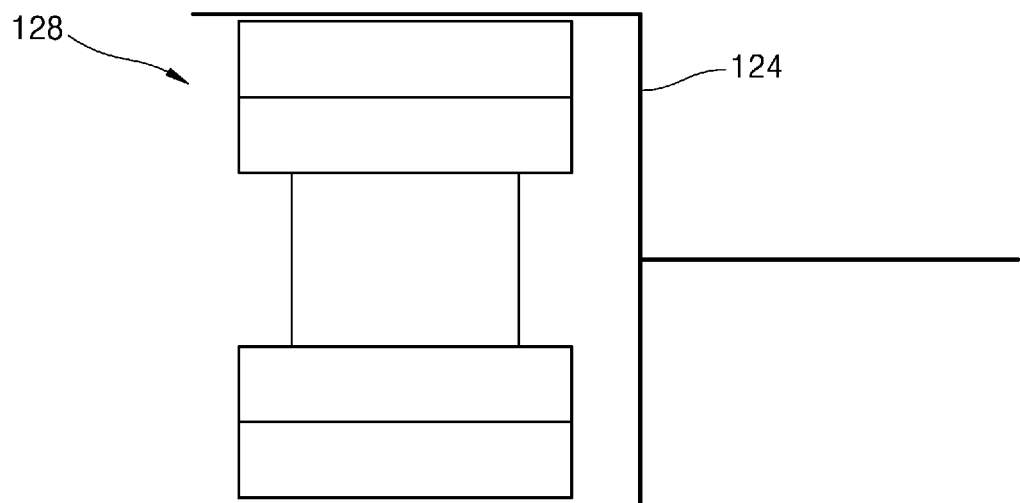
FIGS. 27 to 31 are diagrams showing processes of coupling a fourth pin assembly to a pitch hub.

First, as shown in FIG. 27, the fourth pin assembly 128 is inserted in the pitch hub 124.

Figure 28:
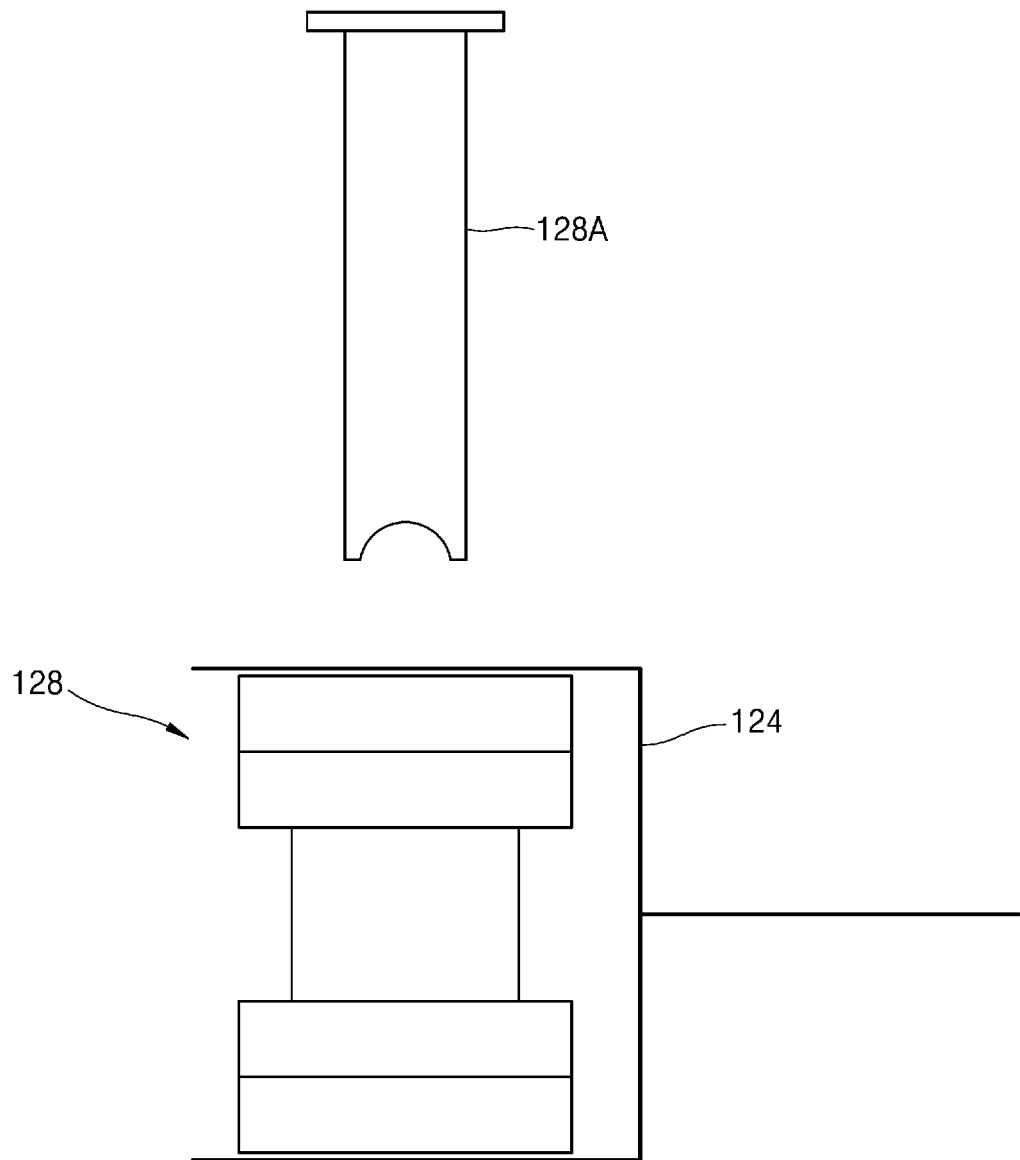
Figure 29:
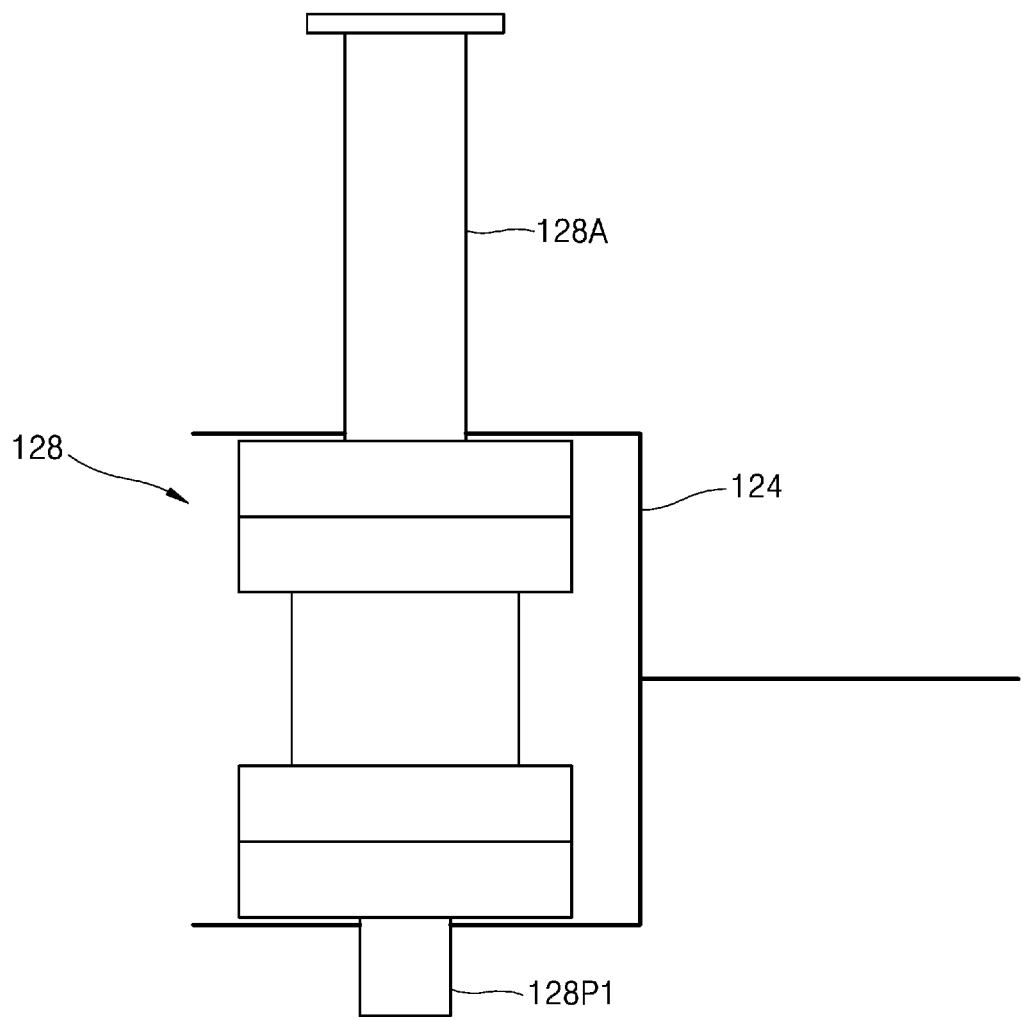
Figure 30:
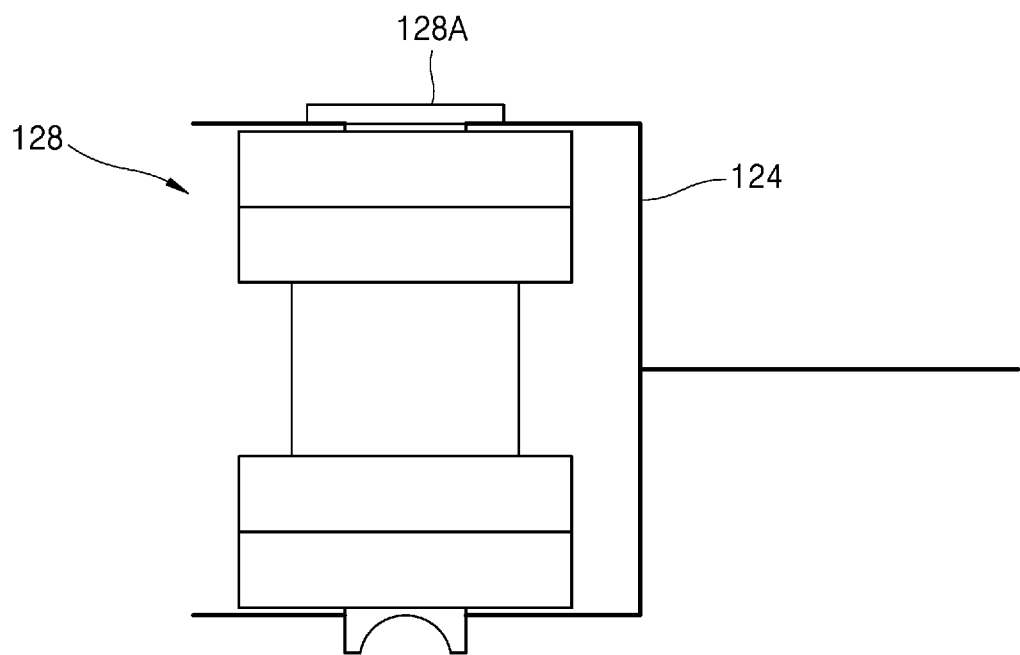

Next, as shown in FIGS. 28 to 30, the fourth pin 128A is inserted in the pitch hub 124 and each of the pulleys while pushing the first replacement pin 128P1. Here, the diameter of the fourth pin 128A is formed to be greater than that of the first replacement pin 128P1 by a certain degree, such that each of the friction reducing members 128B may come into close contact with the groove 1281*out*2.

The fourth pin 128A may be a kind of caulking pin. That is, a flat head is formed at one end of the fourth pin 128A such that the pulley may not be removed, and a recess portion is formed in the other end such that the recess portion is pressed and spread, and the pulley may not be removed.

Figure 31:
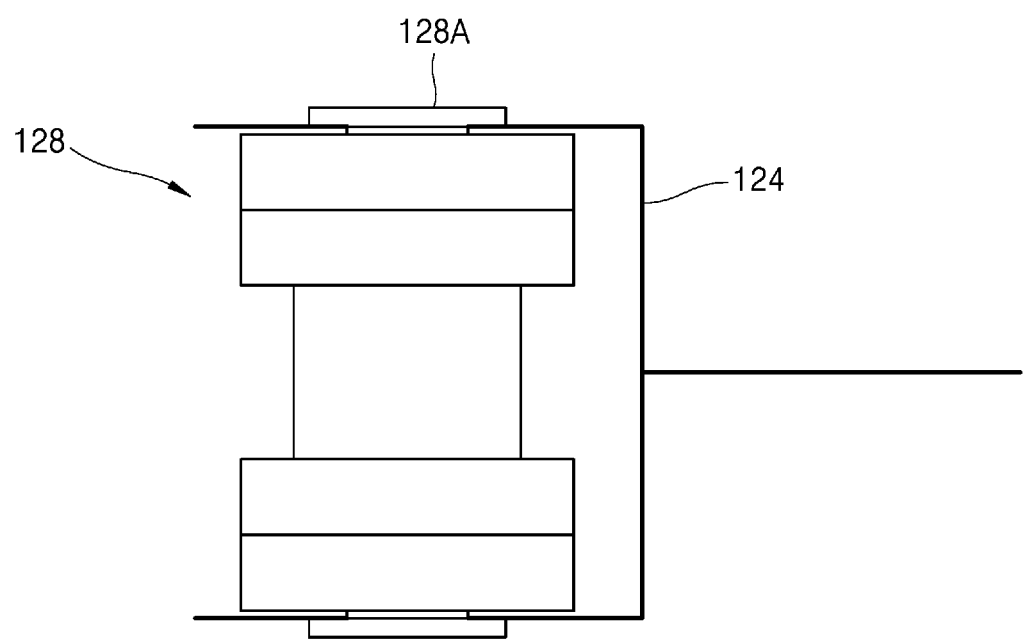

In this state, when a caulking operation is performed, the fourth pin assembly 128 is coupled to the pitch hub 124 by the fourth pin 128A as shown in FIG. 31.

Pin Assembly According to a Second Embodiment

Figure 32:
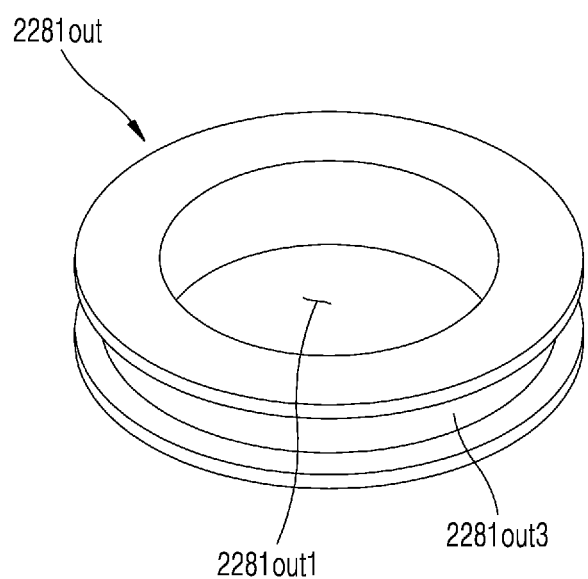
FIG. 32 is a perspective view of a fourth pin first outer pulley of a pin assembly according to a second embodiment of the present disclosure.
Figure 33:
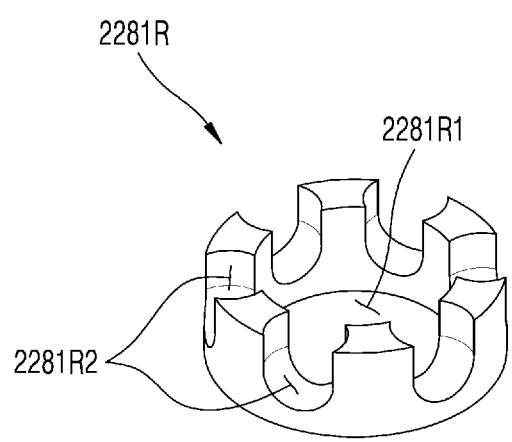
FIG. 33 is a perspective view of a first retainer of a fourth pin in a pin assembly according to the second embodiment of the present disclosure.
Figure 34:
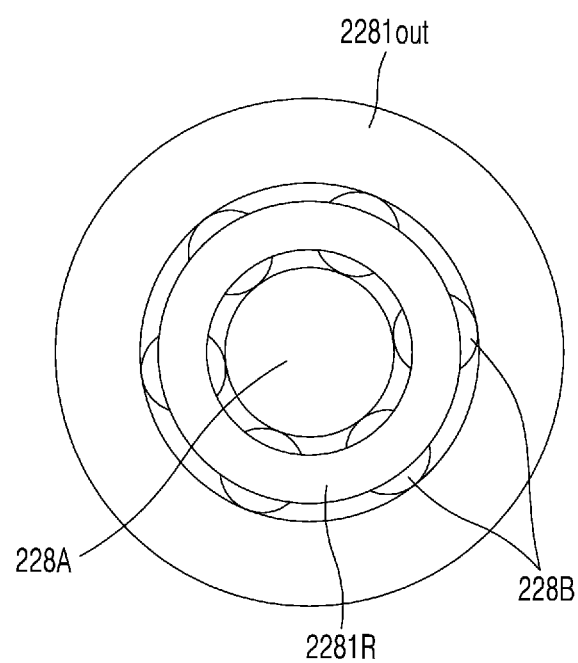
FIG. 34 is a plan view showing a state in which friction reducing members and a retainer are arranged on the fourth pin first outer pulley of FIG. 32.
Figure 35:
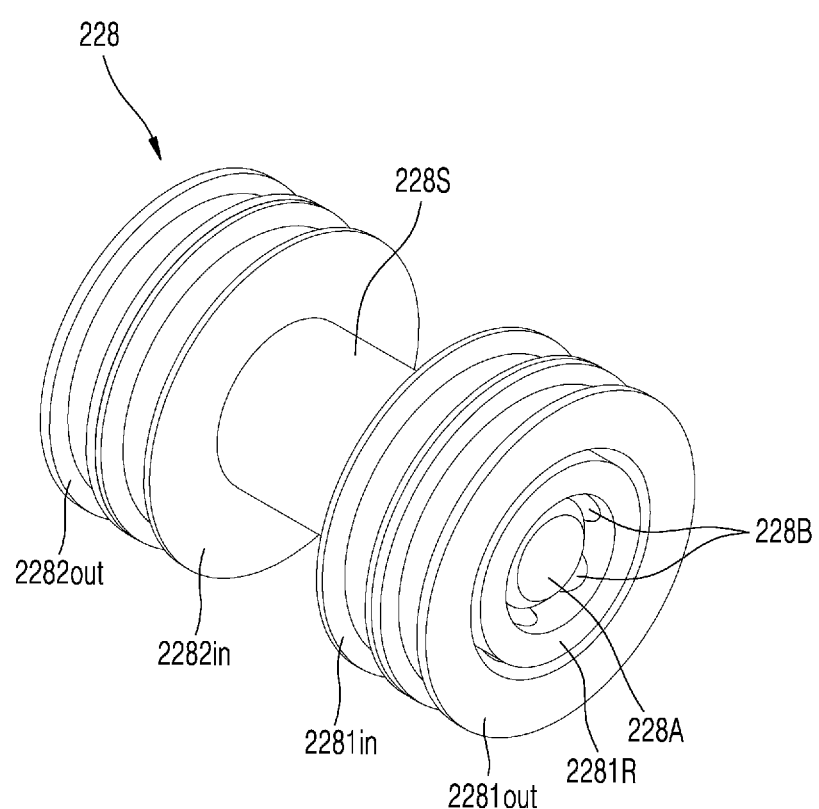
FIG. 35 is a perspective view of a fourth pin assembly of an end tool in a pin assembly according to the second embodiment of the present disclosure.
Figure 36:
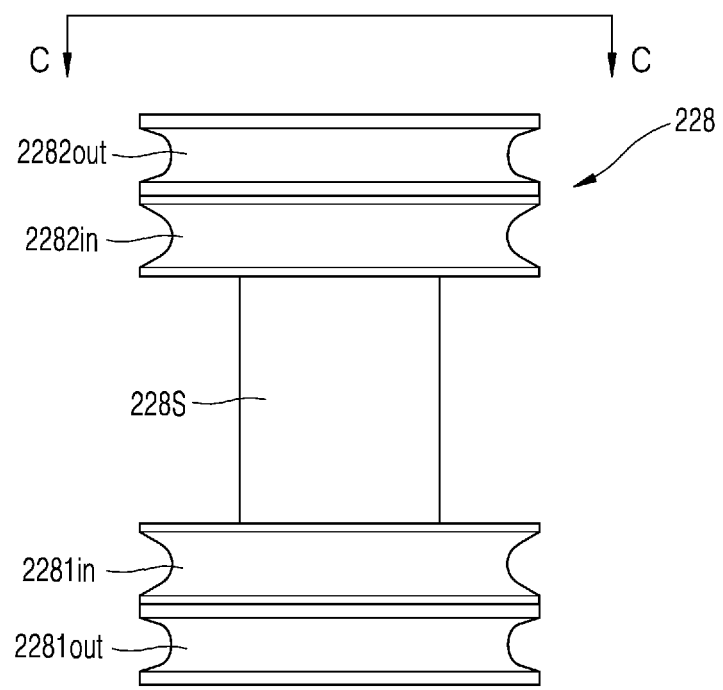
FIG. 36 is a front view of the fourth pin assembly of FIG. 35.
Figure 37:
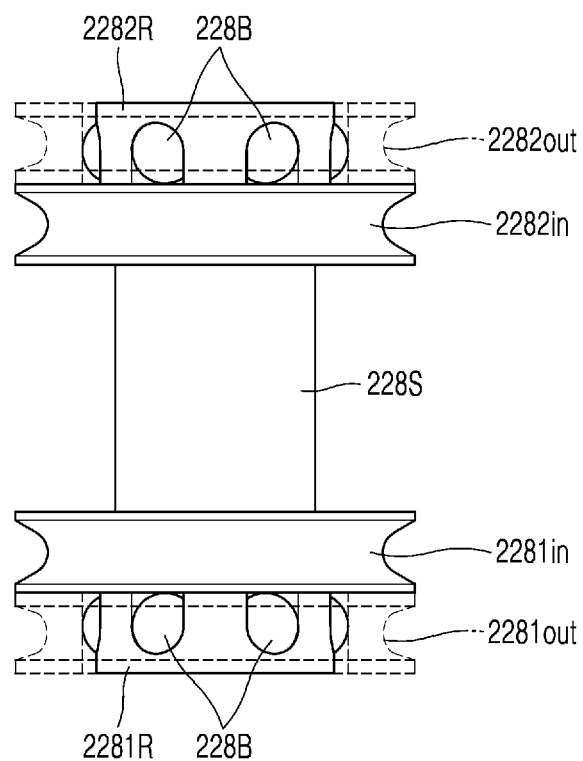
FIG. 37 is a diagram in which some components are indicated by dashed lines in FIG. 36.

FIG. 32 is a perspective view a fourth pin second outer pulley 2282*out* in the pin assembly according to the second embodiment of the present disclosure, FIG. 33 is a perspective view of a fourth pin first retainer 2281R in the pin assembly according to the second embodiment of the present disclosure, and FIG. 34 is a plan view showing a state in which friction reducing members 228B and a retainer 228R are arranged in the fourth pin second outer pulley 2282*out* of FIG. 32. FIG. 35 is a perspective view of a fourth pin assembly 228 of an end tool in the pin assembly according to the second embodiment of the present disclosure, FIG. 36 is a front view of the fourth pin assembly 228 of FIG. 35, and FIG. 37 is a diagram showing some components indicated by dashed lines in FIG. 36.

The pin assembly according to the second embodiment of the present disclosure is different from the first embodiment in view of further including a retainer for fixing balls, instead of fixing the balls in the groove formed in the inner circumferential surface of the outer pulley. Thus, the difference will be described below.

Referring to FIGS. 32 to 37, the fourth pin assembly 228 includes a fourth pin 228A, the fourth pin first outer pulley 2281*out*, a fourth pin first inner pulley 2281*in*, a fourth pin second outer pulley 2282*out*, a fourth pin second inner pulley 2282*in*, and a fourth pin spacer 228S.

Here, the fourth pin first outer pulley 2281*out*, the fourth pin first inner pulley 2281*in*, the fourth pin spacer 228S, the fourth pin second inner pulley 2282*in*, and the fourth pin second outer pulley 2282*out* may be fitted onto the fourth pin 228A therethrough.

Here, a plurality of balls are additionally arranged between the pulley and the pin in the fourth pin first outer pulley 2281*out* and the fourth pin second outer pulley 2282*out* to which a strong force is applied, and function as ball bearings. This will be described below in more detail.

The fourth pin first outer pulley 2281*out* is formed as a loop shape having a hollow portion 2281*out*1 formed therein, and may have a groove 2281*out* 3, on which a wire is to be wound, formed in an outer circumferential surface thereof.

Here, in the present embodiment, in order to prevent the friction reducing members 228B from being removed, the retainer 2281R is formed in the pulley, instead of a groove as in the first embodiment, and inserted among the friction reducing members 228B.

In detail, the retainer 2281R is formed as a loop shape having a hollow portion 2281R1 formed in the center thereof, and one or more friction reducing member accommodation portions 2281R2 are formed in a main body of the retainer. The friction reducing member accommodation portion 2281R2 is formed to have a shape corresponding to at least a part of each friction reducing member 228B, such that each friction reducing member 228B may be inserted in each friction reducing member accommodation portion 2281R2. Thus, removal of the friction reducing member 228B from the fourth pin first outer pulley 2281*out* may be prevented by the friction reducing member accommodation portion 2281R2. That is, the friction reducing member accommodation portions 2281R2 are formed to correspond to the diameters of the friction reducing members 228B, and thus, a part of each friction reducing member 228B is inserted in the friction reducing member accommodation portion 2281R2 such that the friction reducing members 228B may not escape from the fourth pin first outer pulley 2281*out* but remain in the original positions.

Here, in order for the friction reducing members 228B to be inserted in the friction reducing member accommodation portions 2281R2, the diameter of the friction reducing member accommodation portion 2281R2 and the diameter of each of the friction reducing members 228B may be substantially equal to each other, or the diameter of the friction reducing member accommodation portion 2281R2 may be slightly greater than that of each friction reducing member 228B.

Here, the plurality of friction reducing members 228B are arranged in the hollow portion 2281*out*1 of the fourth pin first outer pulley 2281*out*, and the fourth pin 228A is inserted into a central area among the friction reducing members 228B. Therefore, instead of direct contact between the fourth pin 228A and the fourth pin first outer pulley 2281*out*, the fourth pin 228A is in direct contact with the friction reducing members 228B. In order to arrange the friction reducing members 228B as described above, the diameter of the hollow portion 2281*out*1 in the fourth pin first outer pulley 2281*out* may be greater than that of the fourth pin 228A by a certain degree.

As described above, the fourth pin assembly 228 of the present disclosure is basically similar to the ball bearing, but without forming an additional inner wheel, the friction reducing members 228B and the outer circumferential surface of the fourth pin 228A (rotary shaft) come into direct contact with each other. In other words, the fourth pin first outer pulley 2281*out* and the fourth pin 228A are not in direct contact with each other, but the friction reducing members 228B are interposed such that the friction reducing members 228B are in contact with the fourth pin 228A, and thus, the force and friction applied to the pulley and the pin may be distributed in order to implement soft movements, and at the same time, a probability of breakage may be reduced.

In addition, the fourth pin first inner pulley 2281*in* is formed as a loop shape having a hollow portion 2281*in* 1 formed therein. Here, the fourth pin first inner pulley 2281*in* may be a blade pulley that does not have a groove formed in an inner circumferential surface thereof. In addition, a groove 2281*in* 3 for winding a wire may be also formed in an outer circumferential surface of the fourth pin first inner pulley 2281*in*. Here, an additional ball may not be disposed between the fourth pin first inner pulley 2281*in* and the fourth pin 228A. Therefore, the fourth pin first inner pulley 2281*in* and the fourth pin 228A may be in direct contact with each other. To this end, a diameter of the hollow portion of the fourth pin first inner pulley 2281*in* may be substantially equal to or slightly greater than that of the fourth pin 228A.

The spacer 228S is disposed between the fourth pin first inner pulley 2281*in* and the fourth pin second inner pulley 2282*in*, and supports the fourth pin first inner pulley 2281*in* and the fourth pin second inner pulley 2282*in* to maintain a constant gap therebetween. Here, because the spacer 228S is directly fitted onto the fourth pin 228A, an inner diameter of the spacer 228S may be substantially equal to or slightly greater than the diameter of the fourth pin 228A.

The fourth pin second inner pulley 2282*in* is formed to be substantially the same as the fourth pin first inner pulley 2281*in*, and the fourth pin second outer pulley 2282*out* may be formed to be substantially the same as the fourth pin first outer pulley 2281*out*.

As described above, in a state in which the fourth pin assembly 228 is completed by fitting the fourth pin first outer pulley 2281*out*, the fourth pin first inner pulley 2281*in*, the fourth pin spacer 228S, the fourth pin second inner pulley 2282*in*, and the fourth pin second outer pulley 2282*out* sequentially onto the fourth pin 228A, the fourth pin assembly 228 is inserted in the pitch hub (see 124 of FIG. 4). Next, the fourth pin 228A is inserted in the pitch hub (see 124 of FIG. 4) and each pulley while pushing the first replacement pin (see 128P1 of FIG. 27). When the caulking operation is performed in the above state, the fourth pin assembly 228 is coupled to the pitch hub (see 124 of FIG. 4) by the fourth pin 228A. As described above, because the fourth pin assembly 228 is inserted in the pitch hub (see 124 of FIG. 4), the retainer 2281R and the friction reducing members 228B may not be removed to outside due to the pitch hub (see 124 of FIG. 4).

The present disclosure as described above may be seen as an intermediate form between a structure in which a pulley is simply fitted onto a shaft therethrough and a structure in which a ball bearing is fitted onto a shaft. That is, a general ball bearing has an inner ring and an outer ring, but in the present disclosure, the pulley serves as a kind of outer ring of the bearing. In addition, although balls are disposed inside the ball bearing, an additional inner ring is not provided, and the shaft comes into a direct contact with the ball. In addition, in order to prevent the balls from being removed, a groove having a size/shape corresponding to the diameter of the ball is formed in the inner circumferential surface of the pulley.

According to the present disclosure, similar to the ball bearing, the plurality of balls are arranged between the pulley and the shaft, and the load applied to the shaft and the pulley is distributed so that the rotation is performed smoothly. At the same time, because an additional inner ring is not provided, the number of components and manufacturing costs may be reduced, and the internal space corresponding to the width of the inner ring may be saved.

Pin Assembly According to a Third Embodiment

Figure 38:
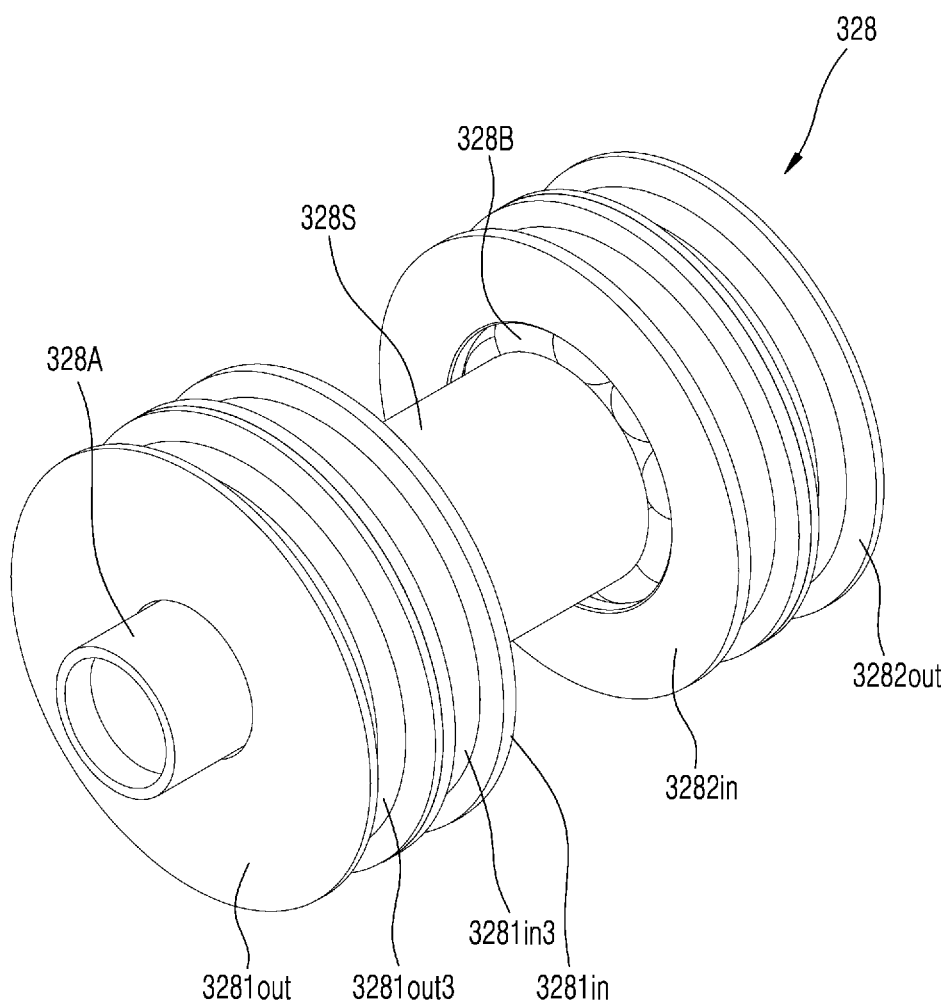
FIG. 38 is a perspective view of a fourth pin assembly according to a third embodiment of the present disclosure.
Figure 39:
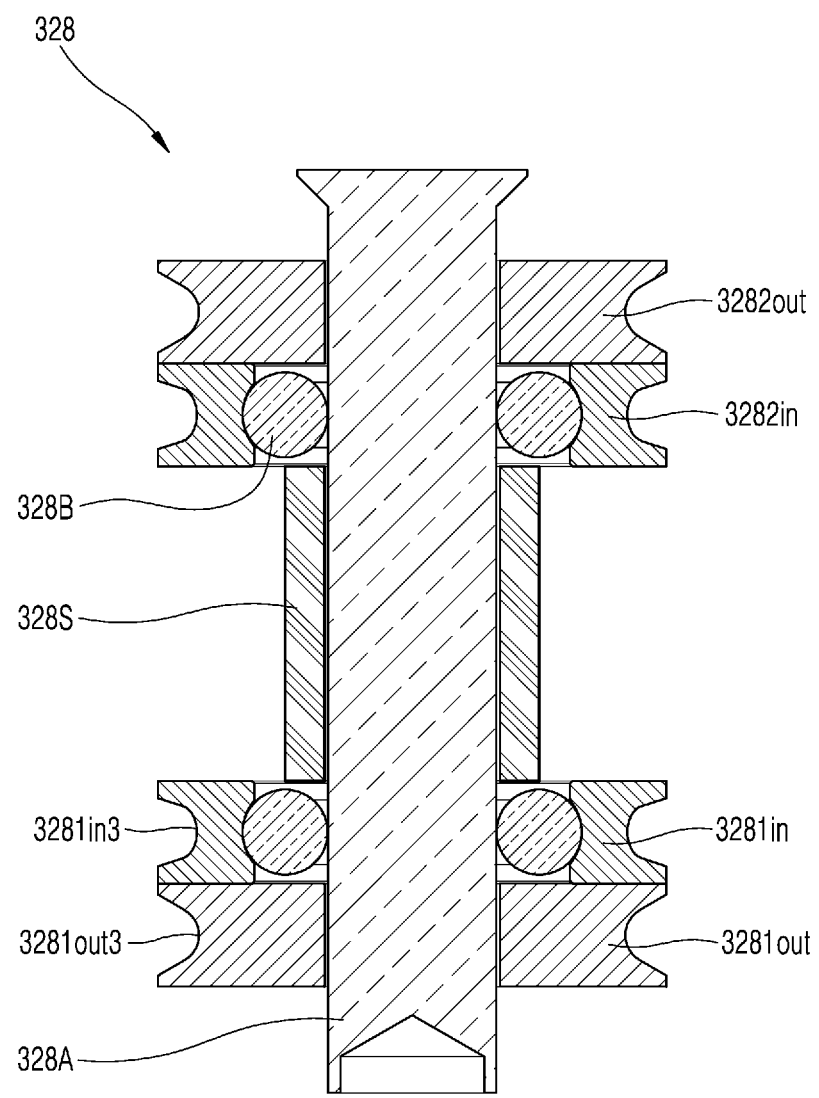
FIG. 39 is a cross-sectional view of the fourth pin assembly of FIG. 38.

FIG. 38 is a perspective view of a fourth pin assembly 328 according to a third embodiment of the present disclosure, and FIG. 39 is a cross-sectional view of the fourth pin assembly 328 of FIG. 38.

As compared with the first embodiment, in the pin assembly according to the third embodiment of the present disclosure, balls are provided in the inner pulley, instead of the outer pulley, and thus, the above difference will be described below.

Referring to FIGS. 38 and 39, the fourth pin assembly 328 according to the third embodiment of the present disclosure includes a fourth pin 328A, a fourth pin first outer pulley 3281*out*, a fourth pin first inner pulley 3281*in*, a fourth pin second outer pulley 3282*out*, a fourth pin second inner pulley 3282*in*, and a fourth pin spacer 328S.

Here, the fourth pin first outer pulley 3281*out*, the fourth pin first inner pulley 3281*in*, the fourth pin spacer 328S, the fourth pin second inner pulley 3282*in*, and the fourth pin second outer pulley 3282*out* may be sequentially fitted onto the fourth pin 328A therethrough.

Here, a plurality of balls are additionally arranged between the pulley and the pin in the fourth pin first inner pulley 3281*in* and the fourth pin second inner pulley 3282*in* and function as ball bearings. This will be described below in more detail.

The fourth pin first inner pulley 3281*in* is formed as a loop shape having the hollow portion (see 1281*out* of FIG. 9) formed therein, and may have the groove (see 1281*out*2 of FIG. 9), in which balls 328B that will be described later are seated, formed in an inner circumferential surface thereof. In addition, a groove 3281*in* 3 for winding a wire may be also formed in an outer circumferential surface of the fourth pin first inner pulley 3281*in*.

Here, at least some parts of the plurality of balls 328B are accommodated in the groove (see 1281*out*2 of FIG. 9) formed in the inner circumferential surface of the fourth pin first inner pulley 3281*in*. When expressed from another point of view, the groove (see 1281*out*2 of FIG. 9) may prevent the balls 328B from being removed from the fourth pin first inner pulley 3281*in*.

Here, the plurality of balls 328B are arranged in the hollow portion (see 1281*out*1 of FIG. 9) of the fourth pin first inner pulley 3281*in*, and the fourth pin 328A is inserted in the central area among the balls 328B. Therefore, instead of direct contact between the fourth pin 328A and the fourth pin first inner pulley 3281*in*, the fourth pin 328A comes into a direct contact with each of the balls 328B.

In addition, the fourth pin first outer pulley 3281*out* is formed as a loop shape having a hollow portion (see 1281*in* 1 of FIG. 19) formed therein. Here, the fourth pin first outer pulley 3281*out* may be a blade pulley that does not have a groove formed in an inner circumferential surface thereof. In addition, a groove 3281*out* 3 on which a wire is to be wound may be also formed in an outer circumferential surface of the fourth pin first outer pulley 3281*out*. Here, an additional ball may not be disposed between the fourth pin first outer pulley 3281*out* and the fourth pin 328A. Therefore, the fourth pin first outer pulley 3281*out* and the fourth pin 328A may be in direct contact with each other.

The fourth pin second inner pulley 3282*in* is formed to be substantially the same as the fourth pin first inner pulley 3281*in*, and the fourth pin second outer pulley 3282*out* may be formed to be substantially the same as the fourth pin first outer pulley 3281*out*.

The present disclosure as described above may be seen as an intermediate form between a structure in which a pulley is simply fitted onto a shaft therethrough and a structure in which a ball bearing is fitted onto a shaft. That is, a general ball bearing has an inner ring and an outer ring, but in the present disclosure, the pulley serves as a kind of outer ring of the bearing. In addition, although balls are arranged inside the ball bearing, an additional inner ring is not provided, and the shaft comes into a direct contact with the ball. In addition, in order to prevent the ball from being removed, a groove having a size/shape corresponding to the diameter of the ball is formed in the inner circumferential surface of the pulley.

According to the present disclosure, similar to the ball bearing, the plurality of balls are arranged between the pulley and the shaft, and the load applied to the shaft and the pulley is distributed so that the rotation is performed smoothly. At the same time, because an additional inner ring is not provided, the number of components and manufacturing costs may be reduced, and the internal space corresponding to the width of the inner ring may be saved.

Pin Assembly According to a Fourth Embodiment

Figure 40:
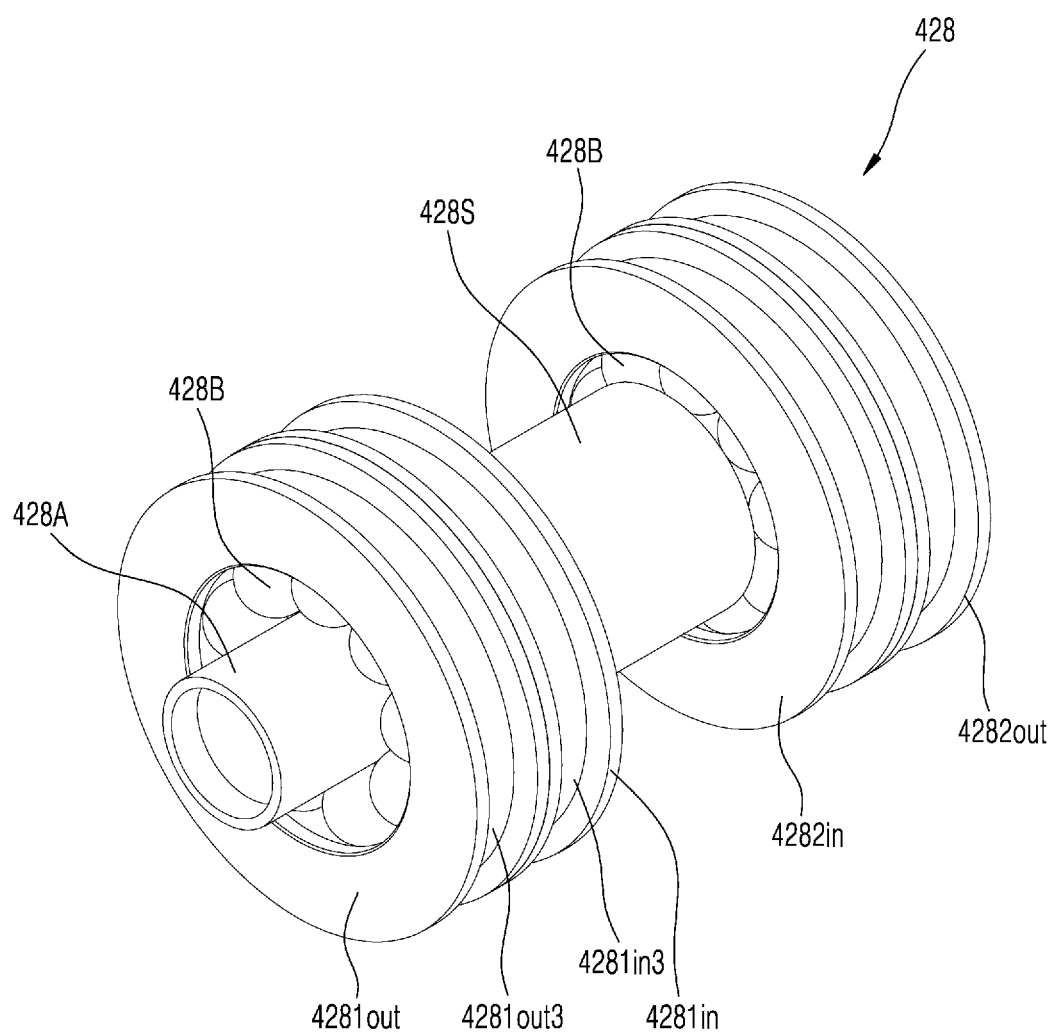
FIG. 40 is a perspective view of a fourth pin assembly according to a fourth embodiment of the present disclosure.
Figure 41:
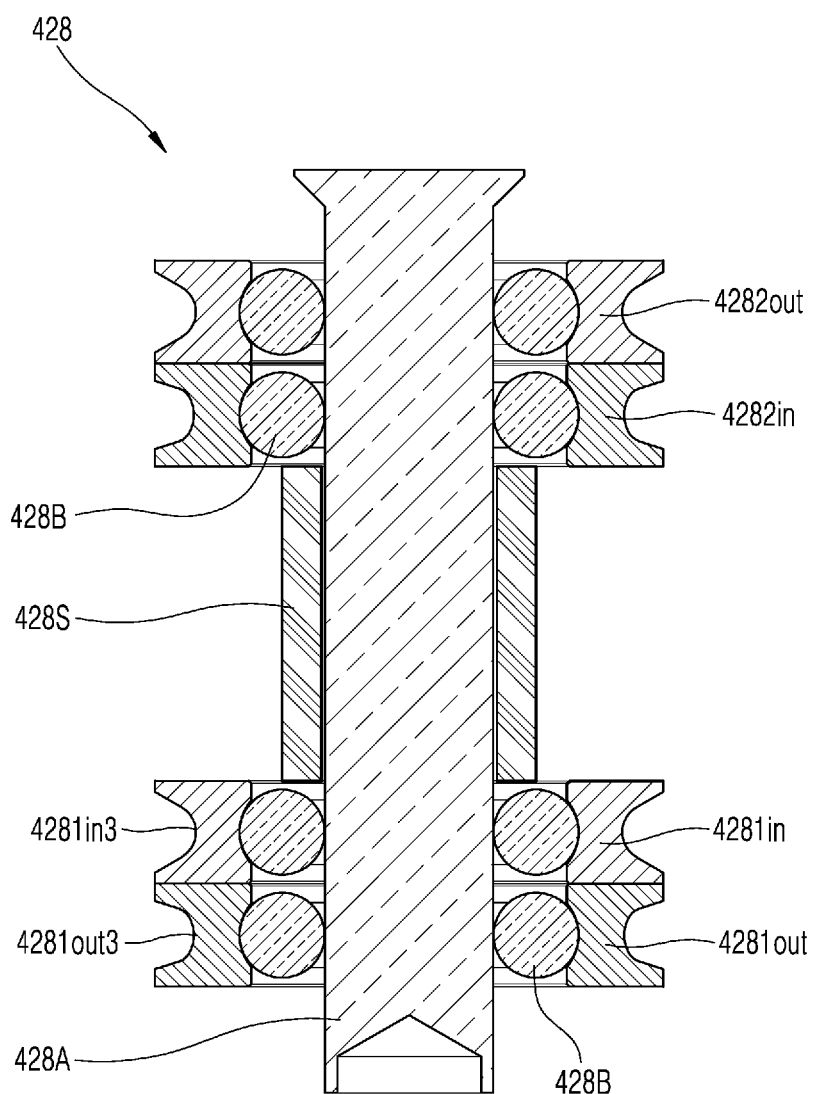
FIG. 41 is a cross-sectional view of the fourth pin assembly of FIG. 40.

FIG. 40 is a perspective view of a fourth pin assembly 428 according to a fourth embodiment of the present disclosure, and FIG. 41 is a cross-sectional view of the fourth pin assembly 428 of FIG. 40.

As compared with the first embodiment, in the pin assembly according to the fourth embodiment of the present disclosure, balls are provided both in the inner pulley and the outer pulley, and thus, the above difference will be described below.

Referring to FIGS. 40 and 41, the fourth pin assembly 428 according to the fourth embodiment of the present disclosure includes a fourth pin 428A, a fourth pin first external 4281*out*, a fourth pin first inner pulley 4281*in*, a fourth pin second outer pulley 4282*out*, a fourth pin second inner pulley 4282*in*, and a fourth pin spacer 428S.

Here, the fourth pin first outer pulley 4281*out*, the fourth pin first inner pulley 4281*in*, the fourth pin spacer 428S, the fourth pin second inner pulley 4282*in*, and the fourth pin second outer pulley 4282*out* may be sequentially fitted onto the fourth pin 428A therethrough.

Here, a plurality of balls are additionally arranged between the pulley and the pin in the fourth pin first inner pulley 4281*in* and the fourth pin second inner pulley 4282*in*, and function as ball bearings. Also, a plurality of balls are additionally arranged between the pulley and the pin in the fourth pin first outer pulley 4281*out* and the fourth pin second outer pulley 4282*out*, and function as ball bearings. This will be described below in more detail.

The fourth pin first inner pulley 4281*in* is formed as a loop shape having the hollow portion (see 1281*out* of FIG. 9) formed therein, and may have the groove (see 1281*out*2 of FIG. 9), in which balls 428B that will be described later are seated, formed in an inner circumferential surface thereof. In addition, a groove 4281*in* 3 on which a wire is to be wound may be also formed in an outer circumferential surface of the fourth pin first inner pulley 4281*in*.

Here, at least some parts of the plurality of balls 428B are accommodated in the groove (see 1281*out*2 of FIG. 9) formed in the inner circumferential surface of the fourth pin first inner pulley 4281*in*. When expressed from another point of view, the groove (see 1281*out*2 of FIG. 9) may prevent the balls 428B from escaping from the fourth pin first inner pulley 4281*in*.

Here, the plurality of balls 428B are arranged in the hollow portion (see 1281*out*1 of FIG. 9) of the fourth pin first inner pulley 4281*in*, and the fourth pin 428A is inserted in the central area among the balls 428B. Therefore, instead of direct contact between the fourth pin 428A and the fourth pin first inner pulley 4281*in*, the fourth pin 428A comes into a direct contact with each of the balls 428B.

The fourth pin second inner pulley 4282*in*, the fourth pin first outer pulley 4281*out*, and the fourth pin second outer pulley 4282*out* may be formed to be substantially identical with the fourth pin first inner pulley 4281*in*.

The present disclosure as described above may be seen as an intermediate form between a structure in which a pulley is simply fitted onto a shaft therethrough and a structure in which a ball bearing is fitted onto a shaft. That is, a general ball bearing has an inner ring and an outer ring, but in the present disclosure, the pulley serves as a kind of outer ring of the bearing. In addition, although a ball is disposed inside the ball bearing, an additional inner ring is not provided, but the shaft is in direct contact with the ball. In addition, in order to prevent the ball from being removed, a groove having a size/shape corresponding to the diameter of the ball is formed in the inner circumferential surface of the pulley.

According to the present disclosure, similar to the ball bearing, the plurality of balls are arranged between the pulley and the shaft, and the load applied to the shaft and the pulley is distributed so that the rotation is performed smoothly. At the same time, because an additional inner ring is not provided, the number of components and manufacturing costs may be reduced, and the internal space corresponding to the width of the inner ring may be saved.

Pin Assembly According to a Fifth Embodiment

Figure 42:
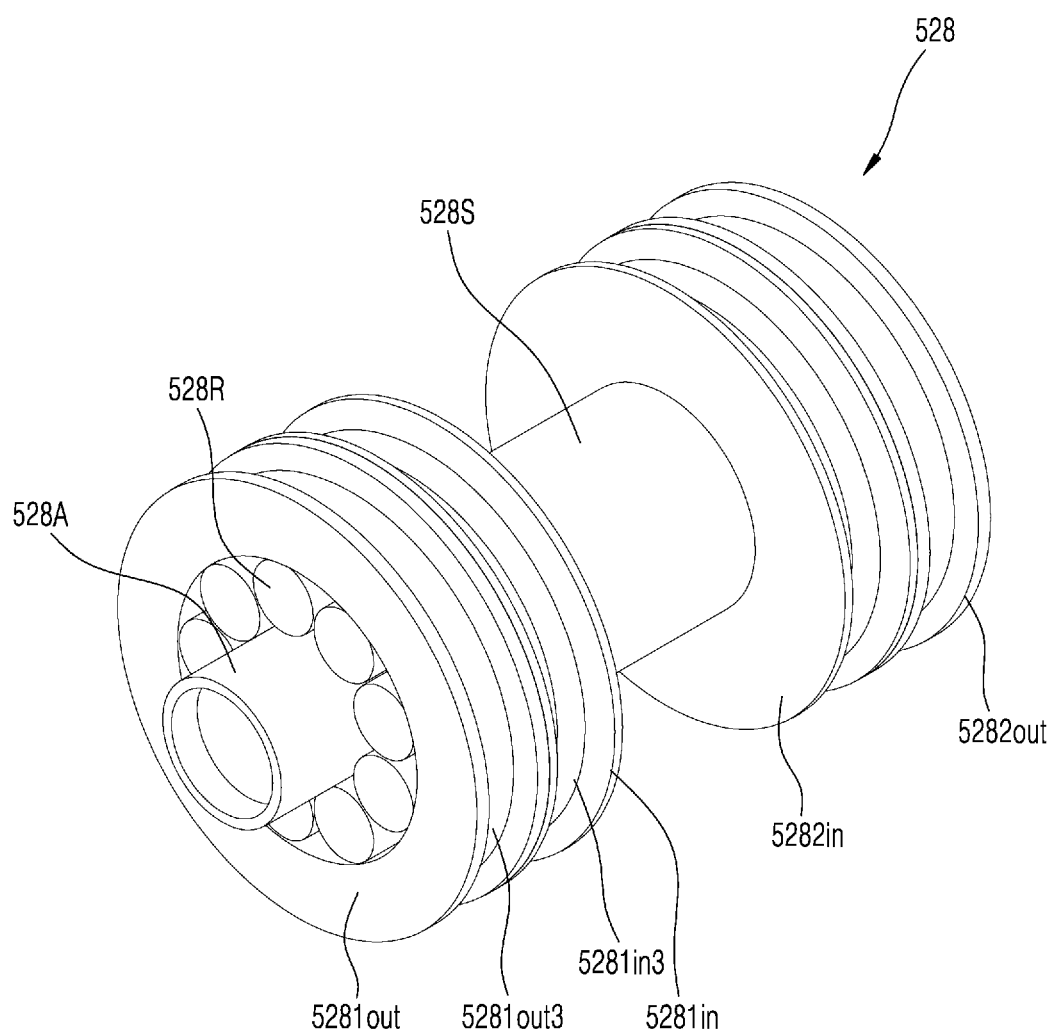
FIG. 42 is a perspective view of a fourth pin assembly according to a fifth embodiment of the present disclosure.
Figure 43:
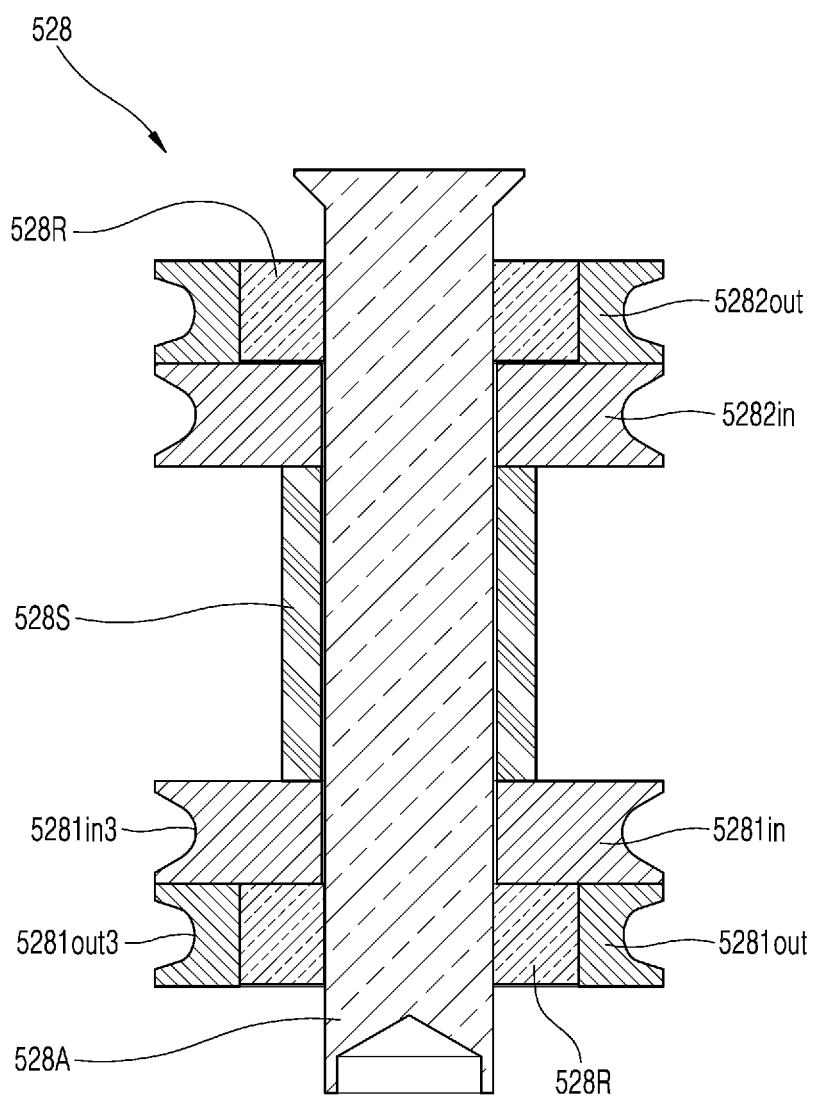
FIG. 43 is a cross-sectional view of the fourth pin assembly of FIG. 42.

FIG. 42 is a perspective view of a fourth pin assembly 528 according to a fifth embodiment of the present disclosure, and FIG. 43 is a cross-sectional view of the fourth pin assembly 528 of FIG. 42.

As compared with the first embodiment, in the pin assembly according to the fifth embodiment of the present disclosure, rollers, instead of the balls, are provided in the outer pulley, and thus, the above difference will be described below.

Referring to FIGS. 42 and 43, the fourth pin assembly 528 according to the fifth embodiment of the present disclosure includes a fourth pin 528A, a fourth pin first external 5281*out*, a fourth pin first inner pulley 5281*in*, a fourth pin second outer pulley 5282*out*, a fourth pin second inner pulley 5282*in*, and a fourth pin spacer 528S.

Here, the fourth pin first outer pulley 5281*out*, the fourth pin first inner pulley 5281*in*, the fourth pin spacer 528S, the fourth pin second inner pulley 5282*in*, and the fourth pin second outer pulley 5282*out* may be sequentially fitted onto the fourth pin 528A therethrough.

Here, a plurality of rollers are additionally arranged between the pulley and the pin in the fourth pin first inner pulley 5281*in* and the fourth pin second inner pulley 5282*in* to which a strong force is applied, and function as roller bearings. This will be described below in more detail.

The fourth pin first outer pulley 5281*out* is formed as a loop shape having a hollow portion 5281*out*1 formed therein. In addition, a groove 5281*out* 3 on which a wire is to be wound may be also formed in an outer circumferential surface of the fourth pin first outer pulley 5281*out*.

Here, the plurality of rollers 528R are arranged in the hollow portion 5281*out*1 of the fourth pin first outer pulley 5281*out*, and the fourth pin 528A is inserted into a central area among the rollers 528R. Therefore, instead of direct contact between the fourth pin 528A and the fourth pin first outer pulley 5281*out*, the fourth pin 528A comes into a direct contact with each of the rollers 528R. To do this, a diameter of the hollow portion 5281*out*1 of the fourth pin first outer pulley 5281*out* may be greater than that of the fourth pin 528A by a certain degree.

As described above, the fourth pin assembly 528 of the present disclosure is basically similar to the roller bearing, but without forming an additional inner wheel, the rollers 528R and the outer circumferential surface of the fourth pin 528A (rotary shaft) are in direct contact with each other. In other words, the fourth pin first outer pulley 5281*out* and the fourth pin 528A are not in direct contact with each other, but the rollers 528R are interposed such that the rollers 528R are in contact with the fourth pin 528A, and thus, the force and friction applied to the pulley and the pin may be distributed in order to implement soft movements, and at the same time, a probability of breakage may be reduced.

In addition, the fourth pin first inner pulley 5281*in* is formed as a loop shape having a hollow portion (see 1281*in* 1 of FIG. 19) formed therein. Here, the fourth pin first inner pulley 5281*in* may be a blade pulley that does not have a groove formed in an inner circumferential surface thereof. In addition, a groove 5281*in* 3 for winding a wire may be also formed on an outer circumferential surface of the fourth pin first inner pulley 5281*in*. Here, an additional ball may not be disposed between the fourth pin first inner pulley 5281*in* and the fourth pin 528A. Therefore, the fourth pin first inner pulley 5281*in* and the fourth pin 528A may be in direct contact with each other. To this end, a diameter of the hollow portion of the fourth pin first inner pulley 5281*in* may be substantially equal to or slightly greater than that of the fourth pin 528A.

The spacer 528S is disposed between the fourth pin first inner pulley 5281*in* and the fourth pin second inner pulley 5282*in*, and supports the fourth pin first inner pulley 5281*in* and the fourth pin second inner pulley 5282*in* to maintain a constant gap therebetween. Here, because the spacer 528S is directly fitted onto the fourth pin 528A, an inner diameter of the spacer 528S may be substantially equal to or slightly greater than the diameter of the fourth pin 528A.

The fourth pin second inner pulley 5282*in* is formed to be substantially the same as the fourth pin first inner pulley 5281*in*, and the fourth pin second outer pulley 5282*out* may be formed to be substantially the same as the fourth pin first outer pulley 5281*out*.

The present disclosure as described above may be seen as an intermediate form between a structure in which a pulley is simply fitted onto a shaft therethrough and a structure in which a roller bearing is fitted onto a shaft. That is, a general roller bearing has an inner ring and an outer ring, but in the present disclosure, the pulley serves as a kind of outer ring of the bearing. In addition, although rollers are disposed inside the ball bearing, an additional inner ring is not provided, and the shaft comes into a direct contact with the roller.

Here, one surface of the fourth pin first outer pulley 5281*out* is blocked by the fourth pin first inner pulley 5281*in*, and the other surface of the fourth pin first outer pulley 5281*out* is blocked by the pitch hub (see 124 of FIG. 31). Thus, removal of the roller from the fourth pin first outer pulley 5281*out* may be prevented.

In addition, in the drawings, the rollers are provided in the outer pulley, but one or more embodiments of the present disclosure are not limited thereto, that is, the rollers may be provided in the inner pulley or may be provided both in the inner pulley and the outer pulley.

According to the present disclosure as described above, a plurality of rollers are arranged between the pulley and the pin (rotary shaft) similarly to the roller bearing, such that the load applied to the pin (rotary shaft) and the pulley is appropriately distributed. Thus, the pulley may be smoothly rotated, and at the same time, an overall durability may be improved. In addition, because a separate inner ring is not provided, the number of components and manufacturing cost are reduced, and moreover, there may be an effect of reducing an inner space corresponding to the width of the inner ring.

According to the present disclosure, a plurality of friction reducing members are arranged between a pulley and a pin (rotary shaft) similarly to a ball bearing such that a load applied to the pin (rotary shaft) and the pulley is appropriately distributed, and thus, the pulley is smoothly rotated and at the same time the overall durability may be improved. In addition, because an additional inner wheel is not provided, the number of components and manufacturing costs are decreased, and moreover, an internal space corresponding to a width of the inner wheel may be saved.

As such, the present disclosure has been described with reference to one embodiment shown in the drawings, but it will be understood that this is merely exemplary, and those of ordinary skill in the art will understand that various modifications and variations of the embodiments are possible therefrom. Accordingly, the true technical protection scope of the present disclosure should be defined by the technical spirit of the appended claims.

The invention claimed is:

1. An end tool of a surgical instrument, the end tool comprising:
    at least one jaw formed to be rotatable;
    an end tool hub in which a first shaft that is a rotating center of the at least one jaw is coupled;
    a pitch hub axially coupled to the end tool hub and provided to be rotatable with respect to the end tool hub; and
    at least one pin assembly coupled to the pitch hub and formed to be rotatable in the pitch hub,
    wherein the at least one pin assembly comprises:
    a pulley formed in a loop shape and having a hollow portion formed therein;
    a pin inserted in the hollow portion of the pulley and performing as a rotary shaft; and
    a plurality of friction reducing members arranged between an inner circumferential surface of the pulley and the pin, the plurality of friction reducing members being in direct contact with both the inner circumferential surface of the pulley and an outer circumferential surface of the pin.

2. The end tool of claim 1, wherein
    the at least one pin assembly includes two pulleys, which include a first outer pulley and a second outer pulley, the two pulleys facing each other, and
    further includes a first inner pulley arranged at an inner side of the first outer pulley and a second inner pulley arranged at an inner side of the second outer pulley.

3. The end tool of claim 2, wherein
the first outer pulley, the first inner pulley, the second inner pulley, and the second outer pulley are sequentially fitted onto the pin therethrough.

4. The end tool of claim 3, wherein
a spacer is additionally interposed between the first inner pulley and the second inner pulley.

5. The end tool of claim 3, wherein
the end tool hub is arranged between the first inner pulley and the second inner pulley.

6. The end tool of claim 2, wherein
the friction reducing members are arranged in the first outer pulley and in the second outer pulley.

7. The end tool of claim 2, wherein
the friction reducing members are arranged in the first inner pulley and in the second inner pulley.

8. The end tool of claim 1, wherein
a groove having a shape corresponding to each of the friction reducing members is formed in an inner circumferential surface of the pulley.

9. The end tool of claim 8, wherein
a radius of the groove formed in the inner circumferential surface of the pulley is equal to or greater than a radius of the friction reducing member.

10. The end tool of claim 8, wherein
each of the friction reducing members is at least partially accommodated in the groove such that the friction reducing member is not removed from the pulley.

11. The end tool of claim 1, further comprising
a retainer formed as a loop shape and having at least one friction reducing member accommodation portion that is formed to have a shape corresponding to at least a part of each friction reducing member in a main body thereof.

12. The end tool of claim 11, wherein
each friction reducing member is inserted in each friction reducing member accommodation portion such that the friction reducing member is not removed from the pulley.

13. The end tool of claim 1, wherein
the friction reducing members include balls.

14. The end tool of claim 1, wherein
the friction reducing members include rollers.

* * * * *